(12) United States Patent
Yu et al.

(10) Patent No.: US 10,973,914 B2
(45) Date of Patent: Apr. 13, 2021

(54) BIVALENT ANTIBODY DIRECTED AGAINST NKG2D AND TUMOR ASSOCIATED ANTIGENS

(71) Applicant: OHIO STATE INNOVATION FOUNDATION, Columbus, OH (US)

(72) Inventors: Jianhua Yu, Columbus, OH (US); Michael Caligiuri, Columbus, OH (US); Wing Keung Chan, Columbus, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 327 days.

(21) Appl. No.: 15/552,078

(22) PCT Filed: Feb. 22, 2016

(86) PCT No.: PCT/US2016/018955
§ 371 (c)(1),
(2) Date: Aug. 18, 2017

(87) PCT Pub. No.: WO2016/134371
PCT Pub. Date: Aug. 25, 2016

(65) Prior Publication Data
US 2018/0237519 A1 Aug. 23, 2018

Related U.S. Application Data

(60) Provisional application No. 62/119,645, filed on Feb. 23, 2015, provisional application No. 62/118,561, filed on Feb. 20, 2015.

(51) Int. Cl.
| | | |
|---|---|---|
| *A61K 39/395* | (2006.01) | |
| *C07K 16/30* | (2006.01) | |
| *C07K 16/46* | (2006.01) | |
| *C07K 16/28* | (2006.01) | |
| *A61P 35/00* | (2006.01) | |
| *A61K 38/17* | (2006.01) | |

(52) U.S. Cl.
CPC ........ *A61K 39/39558* (2013.01); *A61P 35/00* (2018.01); *C07K 16/2803* (2013.01); *C07K 16/2851* (2013.01); *C07K 16/2863* (2013.01); *A61K 38/1774* (2013.01); *C07K 2317/31* (2013.01); *C07K 2317/622* (2013.01); *C07K 2317/73* (2013.01)

(58) Field of Classification Search
CPC ....... A61P 35/00; C07K 16/468; C07K 19/00; A61K 39/39558
See application file for complete search history.

(56) References Cited

U.S. PATENT DOCUMENTS

| | | | |
|---|---|---|---|
| 7,709,610 B2 | 5/2010 | Williams et al. | |
| 10,227,409 B2 | 3/2019 | Yu et al. | |
| 10,358,494 B2 | 7/2019 | Yu et al. | |
| 2004/0038339 A1 | 2/2004 | Kufer et al. | |
| 2006/0210564 A1 | 9/2006 | Kumagai et al. | |
| 2009/0155275 A1* | 6/2009 | Wu ..................... | C07K 16/468 424/136.1 |
| 2011/0044980 A1 | 2/2011 | Ghayur et al. | |
| 2011/0052570 A1 | 3/2011 | Klagsbrun et al. | |
| 2011/0150870 A1 | 6/2011 | Rader et al. | |
| 2012/0003695 A1 | 1/2012 | Davidson et al. | |
| 2012/0034245 A9* | 2/2012 | Thompson ......... | C07K 16/2833 424/179.1 |
| 2012/0064083 A1 | 3/2012 | Williams et al. | |
| 2012/0100162 A1* | 4/2012 | Brodsky .............. | A61K 31/664 424/184.1 |
| 2013/0121915 A1 | 5/2013 | Paas et al. | |
| 2013/0280285 A1 | 10/2013 | Schonfeld | |
| 2014/0037628 A1 | 2/2014 | Morgan et al. | |
| 2014/0178950 A1 | 6/2014 | Solazyme et al. | |
| 2014/0242701 A1 | 8/2014 | Shiku et al. | |
| 2014/0294834 A1 | 10/2014 | Harms et al. | |
| 2014/0302037 A1* | 10/2014 | Borges .................. | C07K 16/28 424/136.1 |

(Continued)

FOREIGN PATENT DOCUMENTS

| | | |
|---|---|---|
| CN | 103113470 A | 5/2013 |
| CN | 103224561 A | 7/2013 |

(Continued)

OTHER PUBLICATIONS

Paul (Fundamental Immunology, 3rd Edition, 1993, pp. 292-295) (Year: 1993).*
Bendig M. M. (Methods: A Companion to Methods in Enzymology, 1995; 8:83-93) (Year: 1995).*
Tabuchi (Breast Cancer Res. Treat, vol. 157, p. 55-63, 2016) (Year: 2016).*
Office Action issued in Chinese application No. 201480030178.9 dated Feb. 19, 2019 including English translation. 12 pages.
Abaza et al. "Effects of amino acid substitutions outside an antigenic site on protein binding to monoclonal antibodies of predetermined specificity obtained by peptide immunization: Demonstration with region 94-100 (antigenic site 3) of myoglobin", (Journal of Protein Chemistry, vol. 11, No. 5, 1992, pp. 433-444).

(Continued)

*Primary Examiner* — Michael Allen
(74) *Attorney, Agent, or Firm* — Foley & Lardner LLP

(57) ABSTRACT

A polypeptide is disclosed that binds tumor-associated antigens (TAA) on the surface of cancer cells and a NKG2D receptor. The NKG2D receptor is expressed on the surfaces of killer cells such as natural killer cells, T cells, natural killer T cells, and gamma delta T cells. In some cases, the TAA is CS-1 or EGFRvIII. Also disclosed are polynucleotides encoding the disclosed polypeptides, vectors comprising the disclosed polynucleotides, and host cells comprising the disclosed vectors. Also disclosed are bivalent antibodies comprising the disclosed polypeptides. Also disclosed are pharmaceutical compositions comprising the disclosed antibodies. Also disclosed are methods of treating cancer in a subject using the disclosed bi-specific antibodies.

14 Claims, 4 Drawing Sheets
Specification includes a Sequence Listing.

(56) References Cited

U.S. PATENT DOCUMENTS

| | | | |
|---|---|---|---|
| 2014/0314667 | A1 | 10/2014 | Hill et al. |
| 2015/0038684 | A1 | 2/2015 | Jensen |
| 2015/0307564 | A1 | 10/2015 | Young et al. |
| 2016/0046724 | A1 | 2/2016 | Brogdon et al. |
| 2016/0331793 | A1 | 11/2016 | Champion et al. |
| 2020/0002418 | A1 | 1/2020 | Yu et al. |

FOREIGN PATENT DOCUMENTS

| | | | |
|---|---|---|---|
| JP | 2012-121878 | | 6/2012 |
| WO | WO-2010/017103 | A2 | 2/2010 |
| WO | 2010/051391 | A1 | 5/2010 |
| WO | WO2010/107658 | * | 9/2010 |
| WO | WO-2011/014659 | | 2/2011 |
| WO | 2012071411 | A2 | 5/2012 |
| WO | 20120714112 | | 5/2012 |
| WO | 2012079000 | | 6/2012 |
| WO | 2013051718 | A1 | 4/2013 |
| WO | WO-2014/138704 | A1 | 9/2014 |
| WO | WO-2014/179759 | A1 | 11/2014 |
| WO | WO-2015/142675 | A2 | 9/2015 |
| WO | WO-2016/154055 | A1 | 9/2016 |
| WO | WO-2016/154585 | A1 | 9/2016 |
| WO | WO-2017/024131 | A1 | 2/2017 |
| WO | WO-2017/079705 | A1 | 5/2017 |
| WO | WO-2018/039247 | A1 | 3/2018 |

OTHER PUBLICATIONS

Attianese, Greta Maria Paola Giordano, et al. "A New Chimeric Antigen Receptor (CAR) Targeting the CD23 Antigen Expressed by Chronic Lymphocytic Leukemia (B-CLL) Cells." (2010): 2446-2446.

Becknell, Brian, et al. "Efficient infection of human natural killer cells with an EBV/retroviral hybrid vector." Journal of immunological methods 296.5 (2005): 115-123.

Benson Jr, Don M., and John C. Byrd. "CS1-directed monoclonal antibody therapy for multiple myeloma." Journal of Clinical Oncology 30.16 (2012): 2013-2014.

Burns, William R., et al. "A high molecular weight melanoma-associated antigen-specific chimeric antigen receptor redirects lymphocytes to target human melanomas." Cancer research 70.8 (2010): 3027-3033.

Caruana, Ignazio, Iulia Diaconu, and Gianpietro Dotti. "From monoclonal antibodies to chimeric antigen receptors for the treatment of human malignancies." Seminars in oncology. vol. 41. No. 5. Elsevier, 2014, pp. 661-666.

Casucci, Monica, et al. "Dual Transgenesis of T Cells with a Novel CD44v6-Specific Chimeric Antigen Receptor and a Suicide Gene for Safe and Effective Targeting of Chemoresistance in Hematopoietic Tumors." Blood. (2011), 2 pages.

Chinnasamy, Dhanalakshmi, et al. "Gene therapy using genetically modified lymphocytes targeting VEGFR-2 inhibits the growth of vascularized syngenic tumors in mice." The Journal of clinical investigation 120.11 (2010): 3953-3968.

Chu, Yaya, et al. "Genetically Engineered Natural Killer (NK) Cell Immunotherapy for Poor Risk B-Cell (CD20+) Leukemia and Lymphoma." (2011): 1003-1003.

Chu, J. et al. (2013). CS1-specific chimeric antigen receptor (CAR)-engineered natural killer cells enhance in vitro and in vivo antitumor activity against human multiple myeloma. Leukemia, 28(4), 917-927.

Chu, J. et al. (2014). Genetic modification of T cells redirected toward CS1 enhances eradication of myeloma cells. Clinical Cancer Research, 20(15), 3989-4000.

Colman et al. "Effects of amino acid sequence changes on antibody-antigen interactions.", (Research in Immunology, 1994; 145(1): 33-36).

European Patent Office, Extended European Search Report issued in European Application No. 14791494.9, dated Nov. 28, 2016, 12 pages.

European Patent Office, Office Action issued in European Application No. 14791494.9, dated Jan. 24, 2018, 9 pages.

Fauriat, C., et al. "Impaired activating receptor expression pattern in natural killer cells from patients with multiple myeloma." Leukemia 20.4 (2006): 732-733.

Francisco, Joseph A., et al. "Agonistic properties and in vivo antitumor activity of the anti-CD40 antibody SGN-14." Cancer research 60.12 (2000): 3225-3231.

Godfrey, James, and Don M. Benson Jr. "The role of natural killer cells in immunity against multiple myeloma." Leukemia & lymphoma 53.9 (2012): 1666-1676.

He, Shun, et al. "MicroRNAs activate natural killer cells through Toll-like receptor signaling." Blood 121.23 (2013): 4663-4671.

Hsi, Eric D., et al. "CS1, a potential new therapeutic antibody target for the treatment of multiple myeloma." Clinical Cancer Research 14.9 (2008): 2775-2784.

Ibragimova and Wade "Stability of the β-Sheet of the WW Domain: A Molecular Dynamics Simulation Study", (Biophysical Journal, Oct. 1999, vol. 77, pp. 2191-2198).

Imai, C., et al. "Chimeric receptors with 4-1BB signaling capacity provoke potent cytotoxicity against acute lymphoblastic leukemia." Leukemia 18.4 (2004): 676-684.

International Searching Authority, International Search Report and Written Opinion from Application No. PCT/US2014/036684, dated Sep. 23, 2014, 11 pages.

Japanese Patent Office, Office Action issued in Japanese Application No. 2016-512083 dated Feb. 20, 2018, 3 pages, Translation Only.

Jena, Bipulendu, Gianpietro Dotti, and Laurence JN Cooper. "Redirecting T-cell specificity by introducing a tumor-specific chimeric antigen receptor." Blood 116.7 (2010): 1035-1044.

Koehler, Heike, et al. "CD28 Costimulation Overcomes Transforming Growth Factor-β-Mediated Repression of Proliferation of Redirected Human CD4+ and CD8+ T Cells in an Antitumor Cell Attack." Cancer research 67.5 (2007): 2265-2273.

Lonial, Sagar, et al. "Elotuzumab in combination with lenalidomide and low-dose dexamethasone in relapsed or refractory multiple myeloma." Journal of clinical oncology 30.16 (2012): 1953-1959.

Ma, J., et al. "Regulation of macrophage activation." Cellular and Molecular Life Sciences 60.11 (2003): 2334-2346.

Maher, John, et al. "Human T-lymphocyte cytotoxicity and proliferation directed by a single chimeric TCRζ/CD28 receptor." Nature biotechnology 20.1 (2002): 70-75.

Martín-Fontecha, Alfonso, et al. "Induced recruitment of NK cells to lymph nodes provides IFN-γ for TH1 priming." Nature immunology 5.12 (2004): 1260-1265.

Mitsiades, Constantine S., et al. "Inhibition of the insulin-like growth factor receptor-1 tyrosine kinase activity as a therapeutic strategy for multiple myeloma, other hematologic malignancies, and solid tumors." Cancer cell 5.3 (2004): 221-230.

Morgan, Richard A., et al. "Case report of a serious adverse event following the administration of T cells transduced with a chimeric antigen receptor recognizing ERBB2." Molecular Therapy 18.4 (2010): 843-851.

Narni-Mancinelli, Emilie, Eric Vivier, and Yann M. Kerdiles. "The 'T-cell-ness' of NK cells: unexpected similarities between NK cells and T cells." International immunology 23.7 (2011): 427-431.

Olson, Janelle A., et al. "NK cells mediate reduction of GVHD by inhibiting activated, alloreactive T cells while retaining GVT effects." Blood 115.21 (2010): 4293-4301.

Palumbo, A., and S. Vincent Rajkumar. "Treatment of newly diagnosed myeloma." Leukemia 23.3 (2009): 449-456.

Phillips, J. H., An My Le, and L. L. Lanier. "Natural killer cells activated in a human mixed lymphocyte response culture identified by expression of Leu-11 and class II histocompatibility antigens." The Journal of experimental medicine 159.4 (1984): 993-1008.

Podar, K., D. Chauhan, and K. C. Anderson. "Bone marrow microenvironment and the identification of new targets for myeloma therapy." Leukemia 23.1 (2009): 10-24.

(56) References Cited

OTHER PUBLICATIONS

Porter, David L., et al. "Chimeric antigen receptor-modified T cells in chronic lymphoid leukemia." New England Journal of Medicine 365.8 (2011): 725-733.
Prazma and Tedder "Dendritic cell CD83: a therapeutic target or innocent bystander?", Immunology Letters 2008, 115: 1-8.
Rosenberg, Steven A., et al. "Use of tumor-infiltrating lymphocytes and interleukin-2 in the immunotherapy of patients with metastatic melanoma." New England Journal of Medicine 319.25 (1988): 1676-1680.
Rudikoff et al. "Single amino acid substitution altering antigen-binding specificity", PNAS USA, 1982, 79: 1979-1983.
Ruggeri, Loredana, et al. "Effectiveness of donor natural killer cell alloreactivity in mismatched hematopoietic transplants." Science 295.5562 (2002): 2097-2100.
Runnels, Judith M., et al. "Optical techniques for tracking multiple myeloma engraftment, growth, and response to therapy." Journal of biomedical optics 16.1 (2011): 011006-011006.
Sadelain, Michel, Isabelle Rivière, and Renier Brentjens. "Targeting tumours with genetically enhanced T lymphocytes." Nature reviews. Cancer 3.1 (2003): 35-45.
Sanchez, C., et al. "Combining T-cell immunotherapy and anti-androgen therapy for prostate cancer." Prostate cancer and prostatic diseases 16.2 (2013), 123-131.
Siegel, Rebecca, Deepa Naishadham, and Ahmedin Jemal. "Cancer statistics, 2013." CA: a cancer journal for clinicians 63.1 (2013): 10-29.
Spits, Hergen, and Lewis L. Lanier. "Natural killer or dendritic: what's in a name?." Immunity 26.1 (2007): 11-16.
Tai, Yu-Tzu, et al. "Anti-CS1 humanized monoclonal antibody HuLuc63 inhibits myeloma cell adhesion and induces antibody-dependent cellular cytotoxicity in the bone marrow milieu." Blood 112.4 (2008): 1329-1337.
Tai, Yu-Tzu, et al. "CS1 promotes multiple myeloma cell adhesion, clonogenic growth, and tumorigenicity via c-maf-mediated interactions with bone marrow stromal cells." Blood 113.18 (2009): 4309-4318.
Topp, Maxx et al., "T-cells from multiple myeloma patients can be rendered to lyse CD138+ multiple myeloma cells by expression of a chimeric immunoreceptor targeting the myeloma-specific antigen HM 1.24" Blood (2003) 102:11, 932a.
Tu, Shui Ping, et al. "IFN-γ inhibits gastric carcinogenesis by inducing epithelial cell autophagy and T-cell apoptosis." Cancer research 71.12 (2011): 4247-4259.
USPTO, Restriction Requirement issued in co-pending U.S. Appl. No. 14/888,877, dated Mar. 14, 2017, 10 pages.
USPTO, Office Action issued in co-pending U.S. Appl. No. 14/888,877, dated Jun. 8, 2017, 22 pages.
USPTO, Office Action issued in co-pending U.S. Appl. No. 14/888,877, dated Nov. 8, 2017, 15 pages.
USPTO, Office Action issued in co-pending U.S. Appl. No. 15/597,436, dated Aug. 25, 2017, 21 pages.
Woof, Jenny M., and Dennis R. Burton. "Human antibody-Fc receptor interactions illuminated by crystal structures." Nature reviews. Immunology 4.2 (2004): 89-99.
Yu, Jianhua, et al. "Pro-and antiinflammatory cytokine signaling: reciprocal antagonism regulates interferon-gamma production by human natural killer cells." Immunity 24.5 (2006): 575-590.
Yu, Jianhua, et al. "CD94 surface density identifies a functional intermediary between the CD56bright and CD56dim human NK-cell subsets." Blood 115.2 (2010): 274-281.
Decision of Final Rejection issued by the Chinese National Intellectual Property Administration in Chinese Application No. 201480030178.9 dated Jul. 8, 2019. 13 pages.
Almagro, Juan C., and Johan Fransson. "Humanization of antibodies." Front Biosci 13.1 (2008): 1619-1633.
Communication pursuant to Rule 71(3). Issued by the European Patent Office in Application No. 14791494.9 dated Feb. 6, 2019. 4 pages.

Gormley, Nicole J. et al., "FDA Drug Approval: Elotuzumab in Combination with Lenalidomide and Dexamethasone for the Treatment of Relapsed or Refractory Multiple Myeloma", clincancerres. aacrjournals.org; Mar. 1, 2017, DOI: 10.1158/1078-0432.CCR-16-2870.
Hammer, Ohad, "CD19 as an attractive target for antibody-based therapy", mAbs 4:5, 571-577; Sep./Oct. 2012; © 2012 Landes Bioscience.
English Translation of Office Action issued by the Japanese Patent Office in Japanese Application No. P-2016-512083 dated Dec. 18, 2018. 3 pages.
Siegel, Rebecca L., Kimberly D. Miller, and Ahmedin Jemal. "Cancer statistics, 2016." CA: a cancer journal for clinicians 66.1 (2016): 7-30.
Notice of Allowance issued by the U.S. Patent and Trademark Office in U.S. Appl. No. 15/597,436 dated Jan. 22, 2019. 16 pages.
Office Action issued by the U.S. Patent and Trademark Office in U.S. Appl. No. 15/597,436. dated Apr. 20, 2018. 42 pages.
Zonder, Jeffrey A. et al., "A phase 1, multicenter, open-label, dose escalation study of elotuzumab in patients with advanced multiple myeloma", Blood Journal, Jul. 19, 2012, vol. 120, No. 3, pp. 552-559.
Office Action issued in Chinese application No. 201480030178.9 dated Feb. 19, 2018, including English translation. 12 pages.
Chinese State Intellectual Property Office. Translation of Office Action dated May 24, 2018 in Chinese Application No. 201480030178.9. 10 pages.
Chu, Yaya & Ayello, Janet & Hochberg, Jessica & Murphy, James & Stier, Andrew & S. Cairo, Mitchell. (2012). Genetically engineered natural killer (NK) cell immunotherapy for poor risk B-cell (CD20+) leukemia and lymphoma (L/L). Cancer Research. 72. 3511-3511.
Extended European Search Report issued by the European Patent Office in Application No. 16753226.6 dated Sep. 4, 2018. 9 pages.
Vyas, Maulik, et al. "Natural ligands and antibody-based fusion proteins: harnessing the immune system against cancer" Trends in molecular medicine 20.2 (2014): 72-82.
Non-Final Office Action issued by the U.S. Patent and Trademark Office in U.S. Appl. No. 15/597,436 dated Oct. 5, 2018. 15 pages.
Non-Final Office Action issued by the U.S. Patent and Trademark Office in U.S. Appl. No. 14/888,877 dated Sep. 26, 2018. 15 pages.
English Translation of Office Action issued by the Patent Office of Israel in Application No. 242315 dated Sep. 17, 2018. 3 pages.
First Examination Report issued by the Australian Intellectual Property Office in Application No. 2014259675 dated Sep. 12, 2018. 3 pages.
International Search Report and Written Opinion issued in Application No. PCT/US2016/018955, dated Aug. 5, 2016.
International Preliminary Report on Patentability issued in Application No. PCT/US2016/018955, dated Aug. 31, 2017.
Schuster, et al., "A phase II, multicenter trial of rindopepimut (CDX-110) in newly diagnosed glioblastoma: the ACT III study", Neuro-Oncology 17(6), 854-861, 2015.
Jakubowiak, et al., "Phase I Trial of Anti-CS1 Monoclonal Antibody Elotuzumab in Combination With Bortezomib in the Treatment of Relapsed/Refractory Multiple Myeloma", J Clinic Oncol 30(16), 1960-5, 2012.
Sentman, "A novel NKG2D-specific Bite cancer immunotherapy", Dartmouth College, Hanover, NH, United States, accessed on-line Feb. 22, 2016, abstract.
Gleason MK, Ross JA, Warlick ED, et al. CD16×CD33 bispecific killer cell engager (BiKE) activates NK cells against primary MDS and MDSC CD33+ targets. Blood. 2014;123(19)3016-3026.
Stamova S, Cartellieri M, Feldmann A, et al. Simultaneous engagement of the activatory receptors NKG2D and CD3 for retargeting of effector cells to CD33-positive malignant cells. Leukemia. 2011;25(6):1053-1056.
Wiernik A, Foley B, Zhang B, et al. Targeting natural killer cells to acute myeloid leukemia in vitro with a CD16×33 bispecific killer cell engager and ADAM17 inhibition. Clin Cancer Res. 2013;19(14):3844-3855.

(56) References Cited

OTHER PUBLICATIONS

Zhang T, Sentman CL. Cancer immunotherapy using a bispecific NK receptor fusion protein that engages both T cells and tumor cells. Cancer Res. 2011;71(6):2066-2076.
Wolf, et al., "BiTEs: bispecific antibody constructs with unique anti-tumor activity", Drug Discovery Today 10(18), 2005, 1237-1244.
Caligiuri et al., "Human natural killer cells", Blood, vol. 112, 2008, pp. 461-469.
Caruso, "Car-Modified Cells Capable of Distinguishing Normal Cells from Malignant Cells", UT GSBS Dissertations and Theses (Open Access), May 2014, 1-205.
Champsaur et al., "Effect of NKG2D ligand expression on host immune responses", Immunological reviews, vol. 235, 2010, pp. 267-285.
Chen et al.,"A combinational therapy of EGFR-CAR NK cells and oncolytic herpes simplex virus 1 for breast cancer brain metastases," Oncotarget, vol. 7, No. 19, Apr. 1, 2016, pp. 27764-27777.
Collins et al., "Elotuzumab directly enhances NK cell cytotoxicity against myeloma via CS1 ligation: evidence for augmented NK cell function complementing ADCC", Cancer Immunol. Immunother., vol. 62, No. 12, Dec. 2013, pp. 1-15.
Congdon et al.,"Epidermal growth factor receptor and variant III targeted immunotherapy," Neuro-Oncology, vol. 16, Jan. 1, 2014, pp. viii20-viii25.
Database Geneseq [Online], "Fusion protein VH-VL of anti-EGFR antibody 528, SEQ ID: 5," retrived from EBI accession No. GSP:AGE14548, XP-002783201, Sep. 6, 2007, 1 page.
Gedeon et al., "An EGFRvIII-targeted bispecific T-cell engager overcomes limitations of the standard of care for glioblastoma", Expert Rev. Clin. Pharamcol., vol. 6, No. 4, Jul. 2013, pp. 1-23.
Groh et al., "Costimulation of CD8alphabeta T cells by NKG2D via engagement by MIC induced on virus-infected cells", Nat. Immunol., vol. 2, 2001, pp. 255-260.
Han et al.,"CAR-Engineered NK Cells Targeting Wild-Type EGFR and EGFRvIII Enhance Killing of Glioblastoma and Patient-Derived Glioblastoma Stem Cells," Scientific Reports, vol. 5, No. 11483, Jul. 9, 2015, pp. 1-13.
Jamieson et al., "The role of the NKG2D immunoreceptor in immune cell activation and natural killing", Immunity, vol. 17, 2002, pp. 19-29.
Johnson et al., "Rational development and characterization of humanized anti-EGFR variant III chimeric antigen receptor T cells for glioblastoma," Science Translational Medicine, vol. 7, No. 275, Feb. 18, 2015, pp. 1-16.
Raulet, "Roles of the NKG2D immunoreceptor and its ligands", Nat. Rev. Immunol., vol. 3, 2003, pp. 781-790.
Schonfeld et al., "Selective Inhibition of Tumor Growth by Clonal NK Cells Expressing an ErbB2/HER2-Specific Chimeric Antigen Receptor", Mol. Ther., vol. 23, No. 2, Dec. 9, 2014, pp. 330-338.
Szmania et al., "Ex vivo-expanded natural killer cells demonstrate robust proliferation in vivo in high-risk relapsed multiple myeloma patients", J. Immunother., vol. 38, 2015, pp. 24-36.
Van De Donk et al., "Monoclonal antibody-based therapy as a new treatment strategy in multiple myeloma", Leukemia, vol. 26, 2012, pp. 199-213.
Vivier et al., "Lymphocyte activation via NKG2D: towards a new paradigm in immune recognition?", Current opinion in immunology, vol. 14, 2002, pp. 306-311.
Zhou et al., "In vitro and in vivo anti-tumor activities of anti-EGFR single-chain variable fragment fused with recombinant gelonin toxin", Journal of Cancer Research and Clinical Oncology. vol. 138, Mar. 7, 2012, pp. 1081-1090.
Zhou et al.,"Cellular Immunotherapy for Carcinoma Using Genetically Modified EGFR-Specific T Lymphocytes," Neoplasia, vol. 15, No. 5, May 2013, pp. 544-553.
Bauer, et al., "Activation of NK Cells and T Cells by NKG2D, a Receptor for Stress-Inducible MICA", Science 285, 727 (1999).
Kwong, et al., "Generation, affinity maturation, and characterization of a human anti-human NKG2D monoclonal antibody with dual antagonistic and agonistic activity", J Mol Biol. Dec. 31, 2008: 384(5): 1143-1156.
Veillette, et al. "CS1, a SLAM family receptor involved in immune regulation, is a therapeutic target in multiple myeloma", Critical Reviews in Oncology/Hematology 88 (2013) 168-177.

* cited by examiner

C: CRUDE PROTEIN EXTRACT
1: PURIFIED anti-CS1 TriCLE

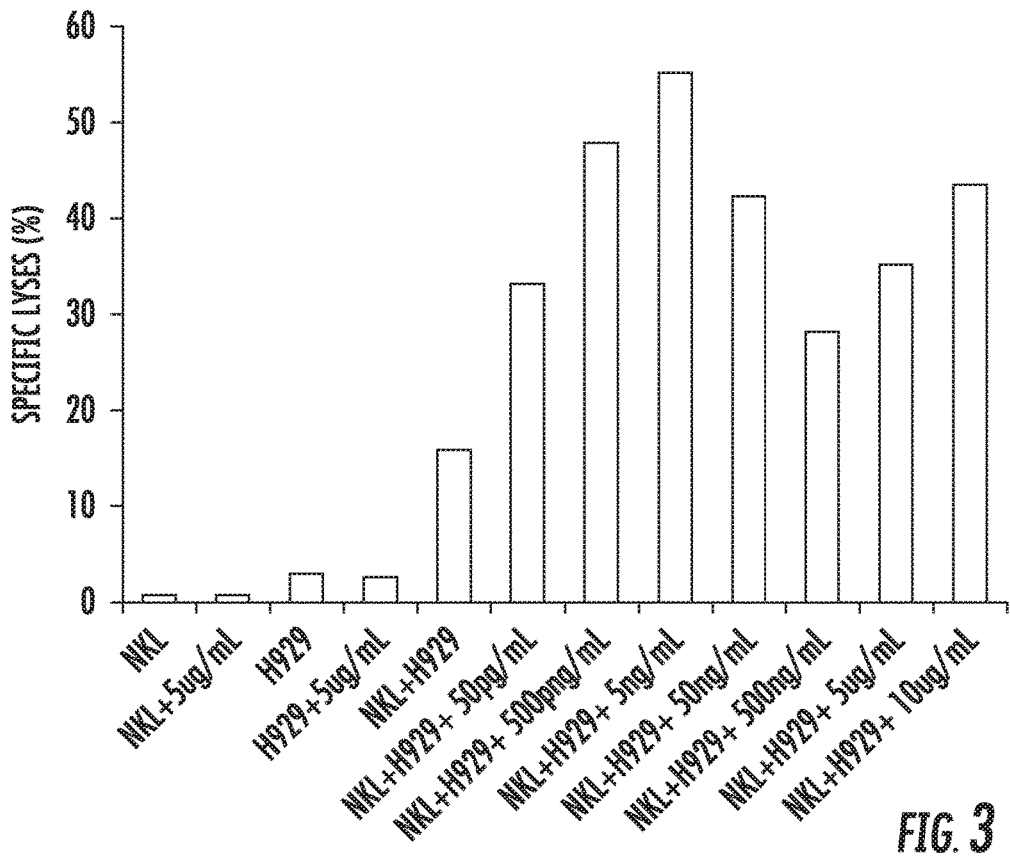
FIG. 3
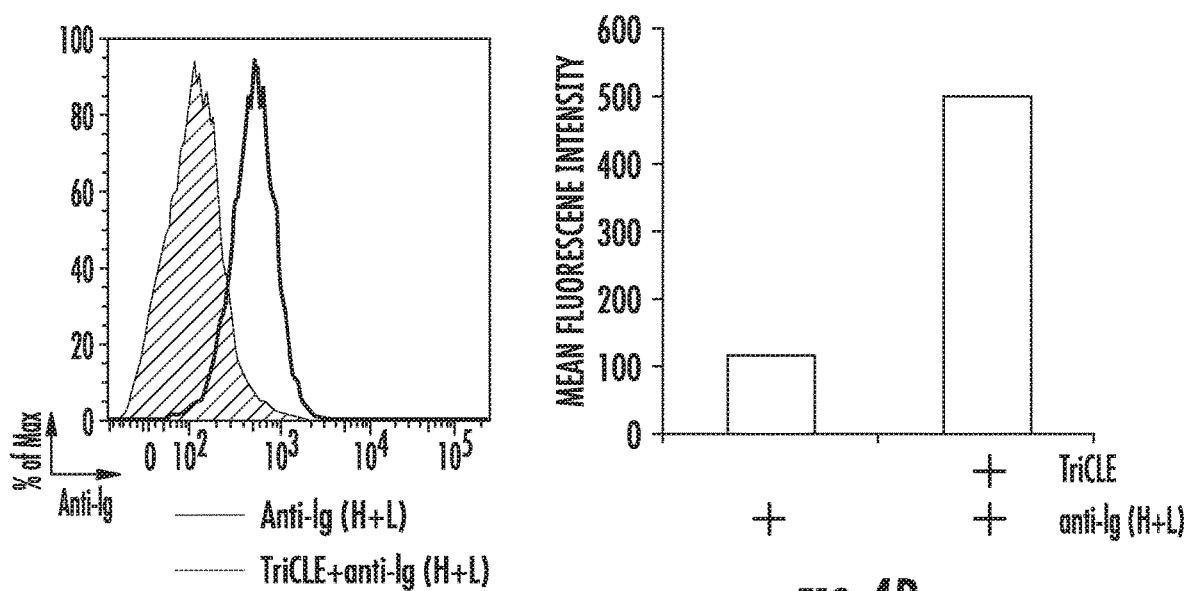
FIG. 4A
FIG. 4B

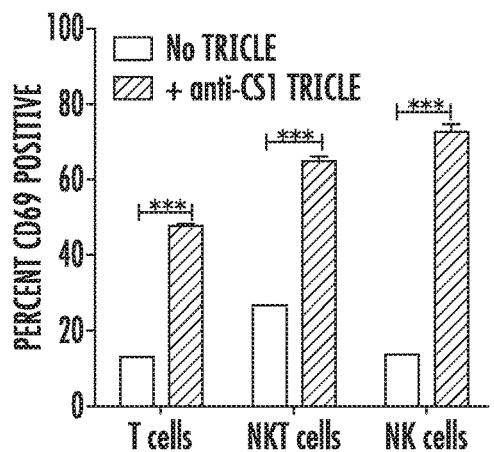 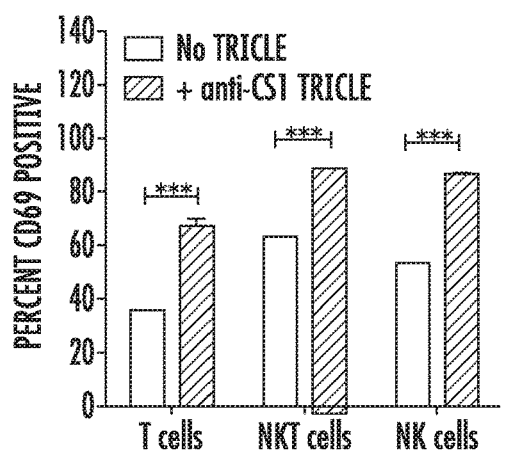
FIG. 5A  FIG. 5B
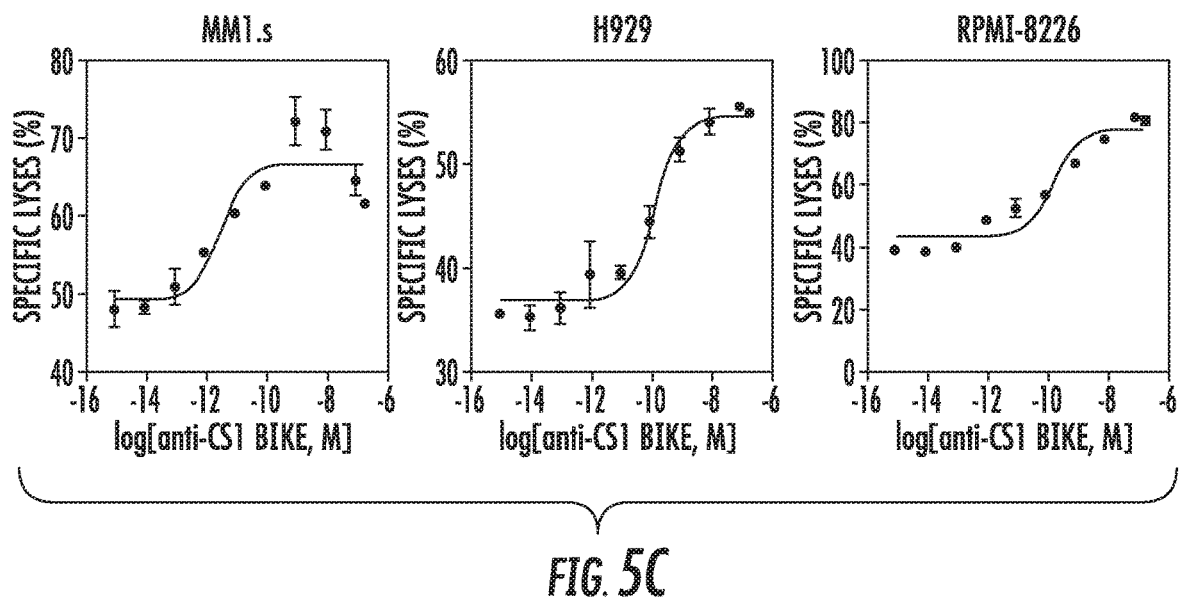
FIG. 5C
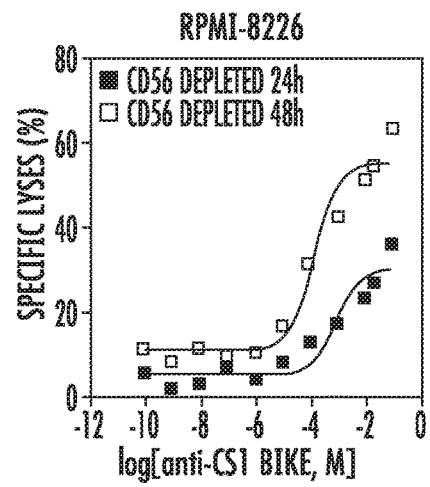
FIG. 5D

BIVALENT ANTIBODY DIRECTED AGAINST NKG2D AND TUMOR ASSOCIATED ANTIGENS

CROSS-REFERENCE TO RELATED APPLICATIONS

This application is a national stage application filed under 35 U.S.C. § 371 of PCT/US2016/018955 filed Feb. 22, 2016, which claims benefit of U.S. Provisional Application No. 62/118,561, filed Feb. 20, 2015, and U.S. Provisional Application No. 62/119,645, filed Feb. 23, 2015, which are hereby incorporated by reference in their entireties.

BACKGROUND

In 2014, there were 1.6 million new cases of cancer diagnosed and 585,720 deaths reported. Current treatment mainly relies on chemotherapy, radiation, surgery and bone marrow transplantation. However, these can be associated with severe side effects, and in some cases the cancer does not respond to the treatments. Thus, new therapeutics are urgently needed. Cancer immunotherapies are promising because they are highly specific and effective in inducing tumor lytic activity from lymphocytes. Fusion proteins such as bi-specific T-cell engagers or bi-specific killer cell engagers (BiTE and BiKE) are cancer immunotherapies that form links between a tumor cell and a T-cell (or natural killer cell, respectively). A BiTE or BiKE protein has two single-chain variable fragments (scFvs) of different antibodies, one of which binds a tumor-specific molecule and the other of which binds a receptor on the surface of the lymphocyte. BiTE and BiKE therapies are expected to have a 100-10,000 fold higher efficacy in tumor cell lysis relative to conventional antibody therapy. However, BiTE therapies specifically target the CD3 receptor on T-cell surfaces, while MIKE therapies target a receptor on the surface of natural killer cells. Currently, no bi specific engager proteins are designed to cross-trigger all killer immune cells, including CD8+ T cells, NK cells, NKT cells, and γδT cells, etc.

SUMMARY

A polypeptide is disclosed that binds a tumor-associated antigens (TAA) and a NKG2D receptor. The polypeptide may comprise an antibody or a fragment thereof that binds to a TAA. In some embodiments, the TAA may be CS-1 or EGFRvIII (the antibody or fragment thus being a "CS-1 antibody" or an "EGFRvIII antibody"). The polypeptide may further comprise an antibody or a fragment thereof that binds to NKG2D receptor ("NKG2D antibody"). The polypeptide may therefore comprise an NKG2D antibody and a CS-1 antibody or an EGFRvIII antibody. On some embodiments, the TAA antibody and/or the NKG2D antibody is a single chain variable fragment (scFv) antibody.

In some embodiments, the polypeptide is a fusion protein expressed by a nucleic acid expressing the TAA antibody and the NKG2D antibody. In some embodiments, the TAA antibody and the NKG2D antibody are separate peptides chemically conjugated together to form the disclosed polypeptide.

In some embodiments of the polypeptide, the TAA antibody and the NKG2D antibody are joined together by a non-immunogenic linker. The non-immunogenic linker may include an amino acid sequence of human muscle aldose protein, a fragment thereof, a variant thereof, or any combination thereof.

NKG2D receptor is expressed by cytotoxic T cells, gamma-delta T cells, natural killer (NK) cells, and NKT cells, which together can be generally referred to herein as "killer cells." NKG2D receptor, upon binding to the protein, can activate the killer cell. Such activation can include the killer cell becoming cytotoxic.

CS-1 is an antigen expressed by multiple myeloma cells. EGFR type III variant (EGFRvIII), has a deletion in its extracellular domain that results in the formation of a new, tumor-specific target found in glioblastoma, as well as in breast, ovarian, prostate, and lung carcinomas.

Accordingly, the disclosed polypeptide can bind to TAAs, such as CS-1 or EGFRvIII, which are expressed by certain cancers, and NKG2D receptor expressed by killer cells. The disclosed polypeptide can bind at the same time TAAs expressed by cancer cells and NKG2D receptor expressed by killer cells, thereby forming a bridge between the cancer cell and the killer cell. Such a bridge can promote the formation of an immunological lytic synapse between the tumor cell and the killer cell. The killer cell can release perforin and/or granzymes over the immunological synapse and thus, induce death of the multiple myeloma cell. Death can include lysis of the cancer cell. As such, the disclosed polypeptide achieves targeted killing of the cancer cell through the recruitment and activation of killer cells.

Also disclosed is a method for treating cancers, such as multiple myeloma, glioblastoma, breast cancer, ovarian cancer, prostate cancer, and lung carcinomas, in a subject in need thereof. The method can include administering the above-described polypeptide to the subject. In some cases, the polypeptide is administered in a therapeutically effective amount.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3 is a graph of the cytotoxicity of NK cell line NKL against multiple myeloma (MM) cell line H929 in the presence of anti-CS-1 TriCLE. Increasing doses of Tri-CLE ranged from 50 pg/mL to 10 ug/mL was added to the coculture of NKL: H929 at effector ratio of 20:1.

FIG. 4A shows binding of TriCLE to CS1$^+$ cell line. 0.2×10$^6$ H929 cells were incubated with TriCLE for 20 min at room temperature. The cells were washed, stained with secondary antibody-binding protein L-biotin and then stained with anti-biotin PE antibody for flow cytometric analysis. Histogram was representative from three independent experiments. FIG. 4B shows a graph comparing the mean fluorescence intensity of the anti-CS-1 TriCLE as primary antibody.

FIG. 5A shows activation of T, NKT and NK cells by TriCLE. 5 ug/mL TriCLE was added to the resting human PBMCs for 4 hours and then the cells were harvested and stained for CD3, CD56, CD14 and CD69 for 20 min at room temperature. The cells were analyzed by flow cytometry. FIG. 5B shows that the anti-CD3 antibody synergized the TriCLE and increased the activation of all three subsets of killer cells. FIG. 5C shows that the cytotoxicity of activated human PBMCs was enhanced by TriCLE against three multiple myeloma cells MM1.s, H929 and RPMI-8226. The EC50 was calculated from the non-linear regression curves. FIG. 5D shows that the anti-CS-1 TriCLE induced cytotoxicity using CD56 depleted effector cells at 24 h and 48 h. ***p<0.001

DETAILED DESCRIPTION

Figure 1:
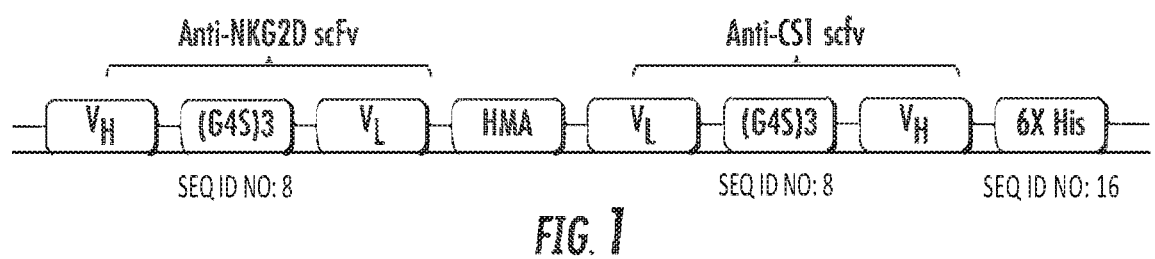
FIG. 1 is a schematic of the anti-CS-1 tri-specific cytotoxic lymphocytes engager (TriCLE) polypeptide design. The anti-CS-1 single chain variable fragment (scFv) and anti-NKG2D scFv are joined together by human muscle aldose (HMA) linker. VH: heavy chain; VL: light chain; (G4S)3 (SEQ ID NO: 8): Glycine-Serine linker; 6XHis (SEQ ID NO: 16): 6 repeats of histidine.

A polypeptide that binds a TAA and the NKG2D receptor. The polypeptide can comprise an antibody or a fragment thereof that binds to a TAA. In one embodiment, such as the one represented by the schematic of FIG. 1A, the TAA can be CS-1 (the antibody or fragment thus being the "CS-1 antibody"). The polypeptide can further comprise an antibody or a fragment thereof that binds to NKG2D receptor ("NKG2D antibody"). The polypeptide can comprise the CS-1 antibody and the NKG2D antibody. The CS-1 antibody and/or the NKG2D antibody can be a single chain variable fragment.

The disclosed polypeptide differs from conventional anti-CD16 BiKE or anti-CD3 BiTE by recruiting the cytotoxicity of all potent killer cells to kill tumor cells (or viral infected cells), leading to superior efficacy without off-target side effects. In some embodiments, the disclosed polypeptide includes an engineered fusion protein of two single chain variable fragments (scFv) targeting NKG2D trigger molecule and tumor-associated antigens (TAA). The NKG2D receptor is an activation molecule highly expressed on cytotoxic T cells, gamma-delta T cells, NK cells and NKT cells, among others. Once the NKG2D receptor is engaged, such as by an anti-NKG2D scFv, antibody, or other ligand, its activation motifs will trigger the phosphylation of other adaptor proteins such as DAP10, and in turn trigger a series of cell activation and execution of cytotoxicity. U.S. Patent Application Publication No. 2010/0150870, which is incorporated by reference, describes antibodies having specificity for human NKG2D and methods of using the same for the treatment of cancer.

The disclosed polypeptide is referred to as tri-specific cytotoxic lymphocytes engager (TriCLE) for its ability to target natural killer cells, T cells, and tumor cells.

TAAs, on the other hand, are expressed on cancer cells. Certain TAAs are cancer-specific. For example, CS-1 is a TAA expressed on multiple myeloma cells. CS1 is a cell surface receptor that belongs to the signaling lymphocytic activation molecule (SLAM) family. The high expression of CS1 on MM cells but not normal cells makes CS1 an attractive target for treatment MM. Preclinical data using elotuzumab, against CS1 showed that elotuzumab exhibited a strong capacity to induce lysis of human MM cell lines when incubated with PBMCs or purified NK cells. EGFRvIII has a deletion in its extracellular domain that results in the formation of a new, tumor-specific target found in glioblastoma, as well as in breast, ovarian, prostate, and lung carcinomas. The antigen-specific nature of the scFvs allows the fusion protein to engage specifically with the NKG2D and the TAA molecules, yielding fewer side effects than current treatment methods.

The disclosed polypeptide can be engineered using recombinant DNA technology. In some embodiments, the polypeptide is a fusion protein expressed by a nucleic acid expressing the TAA antibody and the NKG2D antibody. The DNA sequence coding for the engineered fusion protein can be incorporated into a bacteria expression vector. The disclosed polypeptide can be easily produced, refolded and purified using anion exchange chromatography column. In some embodiments, the TAA antibody and the NKG2D antibody are separate peptides chemically conjugated together to form the disclosed polypeptide.

The scFvs of anti-TAA antibody and anti-NKG2D antibody can be joined and linked together with a non-immunogenic linker. In some embodiments, the linker may be derived from, or be a variant of, the human muscle aldose protein.

When the disclosed polypeptide is administered to a subject with cancer cells expressing the TAA, the anti-TAA scFv binds to the cancer cell surface with one arm and the anti-NKG2D scFv binds to killer cells' NKG2D receptor on the other arm. This engagement will bridge cancer and killer cells, forming immunological lytic synapses. The killer cells can release perforin and granzymes over the synapses, which destroy the cell membrane and induce cell death of the cancer cells. In some embodiments, the anti-TAA scFv is anti-CS-1. In another particular embodiment, the anti-TAA scFv is anti-EGFRvIII. Thus, the disclosed polypeptide can link killer cells to multiple myeloma cells, glioblastoma, breast cancer, ovarian cancer, prostate cancer, and lung carcinomas.

In some embodiments, the disclosed polypeptide comprises a ligand that attaches to NKG2D (i.e., instead of an antibody). Such ligands may be from the MIC or the ULBP For example, the NKG2D ligand may be MICA or MICB, or the NKG2D ligand may be ULBP1, ULBP2, ULBP3, ULBP4, ULBP5, or ULBP6.

In another alternative embodiment, the disclosed polypeptide comprises a ligand (i.e., instead of an antibody) that binds to the TAA, e.g., CS-1 or EGFRvIII.

Also disclosed herein are two nucleic acid constructs, e.g., pGEX6p1m-TriCLE and pET21d-TriCLE, that code for the disclosed polypeptides. The constructs can be used in high yield translation of the protein, using bacterial, mammalian, or fungal cells. The translations can be driven by strong T7 promoters. While the pGEX6p1m and pET21d expression vectors have been found to support efficient protein translation, the scope of the invention includes other expression vectors paired with sequences encoding the fusion proteins disclosed herein.

As used in the specification and claims, the singular form "a," "an," and "the" include plural references unless the context clearly dictates otherwise. For example, the term "a cell" includes a plurality of cells, including mixtures thereof.

The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

The terms "peptide," "protein," and "polypeptide" are used interchangeably to refer to a natural or synthetic molecule comprising two or more amino acids linked by the carboxyl group of one amino acid to the alpha amino group of another. The term "protein" includes amino acids joined to each other by peptide bonds or modified peptide bonds, e.g., peptide isosteres, etc. and can contain modified amino acids other than the 20 gene-encoded amino acids. The polypeptides can be modified by either natural processes, such as post-translational processing, or by chemical modification techniques which are well known in the art.

The term "protein domain" refers to a portion of a protein, portions of a protein, or an entire protein showing structural integrity; this determination may be based on amino acid composition of a portion of a protein, portions of a protein, or the entire protein.

As used herein, "peptidomimetic" means a mimetic of a peptide which includes some alteration of the normal peptide chemistry. Peptidomimetics typically enhance some property of the original peptide, such as increase stability, increased efficacy, enhanced delivery, increased half life, etc. Methods of making peptidomimetics based upon a known polypeptide sequence is described, for example, in U.S. Pat. Nos. 5,631,280; 5,612,895; and 5,579,250. Use of peptidomimetics can involve the incorporation of a non-amino acid residue with non-amide linkages at a given position. One embodiment of the present invention is a peptidomimetic wherein the compound has a bond, a peptide backbone or an amino acid component replaced with a suitable mimic. Some non-limiting examples of unnatural amino acids which can be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

The term "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

The term "antibody" refers to natural or synthetic antibodies that selectively bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that selectively bind the target antigen.

The term "protein fragment" or "antibody fragment" refers to a functional portion of a full-length protein or antibody. When referring to an antibody fragment, the fragment is generally the target binding or variable region. Examples of antibody fragments include Fab, Fab', F(ab')2 and Fv fragments. The phrase "functional fragment or analog" of an antibody is a compound having qualitative biological activity in common with a full-length antibody. For example, a functional fragment or analog of an anti-CS-1 antibody is one which can bind to a CS-1 molecule on a cancer cell surface. As used herein, "functional fragment" with respect to antibodies, refers to Fv, F(ab) and F(ab')2 fragments. An "Fv" fragment is the minimum antibody fragment which contains a complete target recognition and binding site. This region consists of a dimer of one heavy and one light chain variable domain in a tight, non-covalent association $V_H$-$V_L$ dimer). It is in this configuration that the three CDRs of each variable domain interact to define a target binding site on the surface of the $V_H$-$V_L$ dimer. Collectively, the six CDRs confer target binding specificity to the antibody. However, even a single variable domain (scFv, or half of an Fv comprising only three CDRs specific for a target) has the ability to recognize and bind target, although at a lower affinity than the entire binding site.

The terms "CDR", and its plural "CDRs", refer to the complementarity determining region of which three make up the binding character of a light chain variable region (CDR-L1, CDR-L2 and CDR-L3) and three make up the binding character of a heavy chain variable region (CDR-H1, CDR-H2 and CDR-H3). CDRs contain most of the residues responsible for specific interactions of the antibody with the antigen and hence contribute to the functional activity of an antibody molecule: they are the main determinants of antigen specificity.

"Single-chain Fv" or "scFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the sFv to form the desired structure for target binding.

The term "specifically binds", as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity ($K_a$) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule. In some embodiments, the $K_a$ can be from $10^{-6}$ to $10^{-9}$ $M^{-1}$. In other embodiments, the $K_a$ can be from $10^{-9}$ to $10^{-12}$ $M^{-1}$.

A "ligand", as used herein, refers generally to all molecules capable of reacting with or otherwise recognizing or binding to a receptor on a target cell.

Covalent modifications of the disclosed polypeptides constructs are also contemplated, which are generally, but not always, done post-translationally. For example, several types of covalent modifications of the disclosed polypeptides can be introduced into the molecule by reacting specific amino acid residues of the polypeptides construct with an organic derivatizing agent that is capable of reacting with selected side chains or the N- or C-terminal residues.

In some embodiments, the glycosylation pattern of the disclosed polypeptide is altered. As is known in the art, glycosylation patterns can depend on both the sequence of the protein (e.g., the presence or absence of particular glycosylation amino acid residues, discussed below), or the host cell or organism in which the protein is produced. Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used. Another means of increasing the number of carbohydrate moieties is by chemical or enzymatic coupling of glycosides to the protein. These procedures are advantageous in that they do not require production of the protein in a host cell that has glycosylation capabilities for N- and O-linked glycosylation.

In some embodiments, the disclosed polypeptide further comprises one or more labels. The labeling group may be coupled to the disclosed polypeptide via spacer arms of various lengths to reduce potential steric hindrance. Various methods for labeling proteins are known in the art. In general, labels fall into a variety of classes, depending on the assay in which they are to be detected—the following examples include, but are not limited to: a) isotopic labels, which may be radioactive or heavy isotopes, such as radioisotopes or radionuclides (e.g., 3H, 14C, 15N, 35S, 89Zr, 90Y 99Tc, 111In, 125I, 131I); b) magnetic labels (e.g., magnetic particles); c) redox active moieties; d) optical dye (including, but not limited to, chromophores, phosphors and fluorophores) such as fluorescent groups (e.g., FITC, rhodamine, lanthanide phosphors), chetniluminescent groups, and fluorophores which can be either "small molecule" fluores or proteinaceous fluores; e) enzymatic groups (e.g. horseradish peroxidase, β-galactosidase, luciferase, alkaline phosphatase); f) biotinylated groups; g) predetermined polypeptide epitopes recognized by a secondary reporter (e.g., leucine zipper pair sequences, binding sites for secondary antibodies, metal binding domains, epitope tags, etc.), and h) PEGylation.

The disclosed polypeptide may also comprise additional domains that are e.g. helpful in the isolation of the molecule or relate to an adapted pharmacokinetic profile of the molecule. Domains helpful for the isolation of a polypeptide may be selected from peptide motifs or secondarily introduced moieties, which can be captured in an isolation method, e.g. an isolation column.

Non-limiting embodiments of such additional domains comprise peptide motifs known as Myc-tag, HAT-tag, HA-tag, TAP-tag, GST-tag, chitin binding domain (CBD-tag), maltose binding protein (MBP-tag), FLAG®-tag, Strep-tag and variants thereof (e.g. Strep11-tag) and His-tag. In some embodiments, the disclosed polypeptide comprises a His-tag domain, which is generally known as a repeat of consecutive His residues in the amino acid sequence of a molecule, preferably of six His residues.

Amino acid sequence modifications are also contemplated. For example, it may be desirable to improve the binding affinity of the polypeptide, alter the biological properties, or to introduce gain-of-function mutations. Amino acid sequence variants are prepared by introducing appropriate nucleotide changes into the polypeptide's nucleic acid, or by peptide synthesis.

The term "amino acid" or "amino acid residue" typically refers to an amino acid having its art recognized definition such as an amino acid selected from the group consisting of: alanine (Ala or A); arginine (Arg or R); asparagine (Asn or N); aspartic acid (Asp or ID); cysteine (Cys or C); glutamine (Gin or Q); glutamic acid (Glu or E); glycine (Gly or G); histidine (His or H); isoleucine (He or I): leucine (Leu or L); lysine (Lys or K); methionine (Met or M); phenylalanine (Phe or F); pro line (Pro or P); serine (Ser or S); threonine (Thr or T); tryptophan (Trp or W); tyrosine (Tyr or Y); and valine (Val or V), although modified, synthetic, or rare amino acids may be used as desired. Generally, amino acids can be grouped as having a nonpolar side chain (e.g., Ala, Cys, He, Leu, Met, Phe, Pro, Val); a negatively charged side chain (e.g., Asp, Glu); a positively charged sidechain (e.g., Arg, His, Lys); or an uncharged polar side chain (e.g., Asn, Cys, Gin, Gly, His, Met, Phe, Ser, Thr, Trp, and Tyr).

Amino acid modifications include, for example, deletions from, and/or insertions into, and/or substitutions of, residues within the amino acid sequences of the antibody constructs. Any combination of deletion, insertion, and substitution is made to arrive at the final construct, provided that the final construct possesses the desired characteristics. The amino acid changes also may alter post-translational processes of the disclosed polypeptide, such as changing the number or position of glycosylation sites.

For example, 1, 2, 3, 4, 5, or 6 amino acids may be inserted or deleted in each of the CDRs (of course, dependent on their length). An insertional variant of the disclosed polypeptide includes a fusion to the N-terminus or to the C-terminus of the disclosed polypeptide to an enzyme or a fusion to a polypeptide which increases the serum half-life of the disclosed polypeptide.

The sites of greatest interest for substitutional mutagenesis include the CDRs of the heavy and/or light chain, in particular the hypervariable regions. The substitutions are preferably conservative substitutions as described herein. Preferably, 1, 2, 3, 4, 5, 6, 7, 8, 9, or 10 amino acids may be substituted in a CDR, while 1, 2, 3, 4, 5, 6, 7, 8, 9, 10, 11, 12, 13, 14, 15, 16, 17, 18, 19, 20, or 25 amino acids may be substituted in the framework regions (FRs), depending on the length of the CDR or FR. For example, if a CDR sequence encompasses 6 amino acids, it is envisaged that one, two or three of these amino acids are substituted. Similarly, if a CDR sequence encompasses 15 amino acids it is envisaged that one, two, three, four, five or six of these amino acids are substituted.

A useful method for identification of certain residues or regions of the antibody constructs that are preferred locations for mutagenesis is called "alanine scanning mutagenesis" as described by Cunningham and Wells in Science, 244: 1081-1085 (1989). Here, a residue or group of target residues within the antibody construct is/are identified (e.g. charged residues such as arg, asp, his, lys, and glu) and replaced by a neutral or negatively charged amino acid (most preferably alanine or polyalanine) to affect the interaction of the amino acids with the epitope.

Those amino acid locations demonstrating functional sensitivity to the substitutions then are refined by introducing further or other variants at, or for, the sites of substitution. Thus, while the site or region for introducing an amino acid sequence variation is predetermined, the nature of the mutation per se needs not to be predetermined. For example, to analyze or optimize the performance of a mutation at a given site, alanine scanning or random mutagenesis may be conducted at a target codon or region, and the expressed antibody construct variants are screened for the optimal combination of desired activity. Techniques for making substitution mutations at predetermined sites in the DNA having a known sequence are well known, for example, M13 primer mutagenesis and PCR mutagenesis. Screening of the mutants is done using assays of target antigen binding activities.

Also disclosed are variants of the disclosed polypeptides having conservative amino acid substitutions, non-conservative amino acid substitutions (i.e. a degenerate variant), substitutions within the wobble position of each codon (i.e. DNA and RNA) encoding an amino acid, amino acids added to the C-terminus of a peptide, or a peptide having 60%, 70%, 80%, 90%, or 95% homology to a reference sequence.

The term "percent (%) sequence identity" or "homology" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity.

Generally, if amino acids are substituted in one or more or all of the CDRs of the heavy and/or light chain, it is preferred that the then-obtained "substituted" sequence is at least 60%, 65%, 70%, 75%, 80%, 90%, 95% identical to the "original" CDR sequence. This means that it is dependent of the length of the CDR to which degree it is identical to the "substituted" sequence. For example, a CDR having 5 amino acids can be 80% identical to its substituted sequence in order to have at least one amino acid substituted. Accordingly, the CDRs of the antibody construct may have different degrees of identity to their substituted sequences, e.g., CDRL1 may have 80%, while CDRL3 may have 90%.

In some cases, the substitutions (or replacements) are conservative substitutions. However, any substitution is envisaged as long as the antibody construct retains its capability to bind to NKG2D via the first binding domain and to a TAA, such as CS-1 or EGFRvIII, via the second binding domain.

For amino acid sequences, sequence identity and/or similarity is determined by using standard techniques known in the art, including, but not limited to, the local sequence identity algorithm of Smith and Waterman, 1981, Adv. Appl. Math. 2:482, the sequence identity alignment algorithm of Needleman and Wunsch, 1970, J. Mol. Biol. 48:443, the search for similarity method of Pearson and Lipman, 1988, Proc. Nat. Acad. Sci. U.S.A. 85:2444, computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et a/., 1984, Nucl. Acid Res. 12:387-395, preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc. An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, 1987, J. Mol. Evol. 35:351-360; the method is similar to that described by Higgins and Sharp, 1989, CABIOS 5:151-153. Useful PILEUP parameters including a default gap weight of 3.00, a default gap length weight of 0.10, and weighted end gaps.

Another example of a useful algorithm is the BLAST algorithm, described in: Altschul et al., 1990, J. Mol. Biol. 215:403-410; Altschul et al., 1997, Nucleic Acids Res. 25:3389-3402; and Karin et al., 1993, Proc. Natl. Acad. Sci. U.S.A. 90:5873-5787. A particularly useful BLAST program is the WU-BLAST-2 program which was obtained from Altschul of al., 1996, Methods in Enzymology 266: 460-480. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., 1993, Nucl. Acids Res. 25:3389-3402. Gapped BLAST uses BLOSUM-62 substitution scores; threshold T parameter set to 9; the two-hit method to trigger ungapped extensions, charges gap lengths of k a cost of 10+k; Xu set to 16, and Xg set to 40 for database search stage and to 67 for the output stage of the algorithms. Gapped alignments are triggered by a score corresponding to about 22 bits.

Generally, the amino acid homology, similarity, or identity between individual variant CDRs are at least 60% to the sequences depicted herein, and more typically with preferably increasing homologies or identities of at least 65% or 70%, more preferably at least 75% or 80%, even more preferably at least 85%, 90%, 91%, 92%, 93%, 94%, 95%, 96%, 97%, 98%, 99%, and almost 100%. In a similar manner, "percent (%) nucleic acid sequence identity" with respect to the nucleic acid sequence of the binding proteins identified herein is defined as the percentage of nucleotide residues in a candidate sequence that are identical with the nucleotide residues in the coding sequence of the antibody construct. A specific method utilizes the BLASTN module of WU-BLAST-2 set to the default parameters, with overlap span and overlap fraction set to 1 and 0.125, respectively.

Generally, the nucleic acid sequence homology, similarity, or identity between the nucleotide sequences encoding individual variant CDRs and the nucleotide sequences depicted herein are at least 60%, and more typically with preferably increasing homologies or identities of at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99%, and almost 100%. Thus, a "variant CDR" is one with the specified homology, similarity, or identity to the parent CDR of the invention, and shares biological function, including, but not limited to, at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of the parent CDR.

In some embodiments, the disclosed polypeptide is a bi-specific single chain antibody having the following formula:

$V_LN-V_HN-V_LT-V_HT$, $V_HN-V_LN-V_HT-V_LT$,

V$_L$N-V$_H$N-V$_H$T-V$_L$T, or

V$_H$N-V$_L$N-V$_L$T-V$_H$T, wherein "V$_H$N" is a heavy chain variable domain specific for NKG2D;

wherein "V$_L$N" is a light chain variable domain specific for NKG2D;

wherein "V$_H$T" is a heavy chain variable domain specific for a tumor cell antigen;

wherein "V$_L$T" is a light chain variable domain specific for the tumor cell antigen;

wherein "-" consists of a peptide linker or a peptide bond; and wherein "-" consists of a peptide linker or a peptide bond.

Note that the above formula does not specify direction and therefore contemplates that either end can be the amino terminus or the carboxy terminus.

In some embodiments, the tumor cell antigen is CS-1 or EGFRvIII.

In some embodiments, V$_H$N comprises the amino acid sequence SEQ ID NO:5, and V$_L$N. comprises the amino acid sequence SEQ ID NO:0:6. In some embodiments, V$_H$T comprises the amino acid sequence SEQ ID NO:13 and V$_L$T comprises the amino acid sequence SEQ ID NO:14. In some embodiments, V$_H$T comprises the amino acid sequence SEQ ID NO:19 and V$_L$T comprises the amino acid sequence SEQ ID NO:20. In some embodiments, the "-" linker comprises the amino acid sequence SEQ ID NO:8, in some embodiments, the "-" linker comprises the amino acid sequence SEQ ID NO:10. For any of these embodiments, the specified sequences may be modified to improve the binding affinity of the polypeptide, alter the biological properties, or to introduce gain-of-function mutations. For example, in some embodiments, the above sequences can contain 1, 2, 3, 4, or 5 amino acid substitutions, such as conservative substitutions, that maintain or improve binding affinity.

In some embodiments, the polypeptide comprises the amino acid sequence SEQ ID NO:21.

Bispecific antibodies can be constructed using only antibody variable domains. A fairly efficient and relatively simple method is to make the linker sequence between the V$_H$ and V$_L$ domains so short that they cannot fold over and bind one another. Reduction of the linker length to 3-12 residues prevents the monomeric configuration of the scFv molecule and favors intermolecular V$_H$-V$_L$ pairings with formation of a 60 kDa non-covalent scFv dimer "diabody". The diabody format can also be used for generation of recombinant bi-specific antibodies, which are obtained by the noncovalent association of two single-chain fusion products, consisting of the V$_H$ domain from one antibody connected by a short linker to the V$_L$ domain of another antibody. Reducing the linker length still further below three residues can result in the formation of trimers ("triabody", about 90 kDa) or tetramers ("tetrabody", about 120 kDa). For a review of engineered antibodies, particularly single domain fragments, see Holliger and Hudson, 2005, Nature Biotechnology, 23:1126-1136. All of such engineered antibodies can be used in the fusion polypeptides provided herein.

Tetravalent TANDAB® (tandem diabody) can be prepared substantially as described in WO 1999057150 A3 or US20060233787, which are incorporated by reference for the teaching of methods of making TANDAB® molecules.

The antigen recognition sites or entire variable regions of the engineered antibodies can be derived from one or more parental antibodies directed against any antigen of interest (e.g., CS-1). The parental antibodies can include naturally occurring antibodies or antibody fragments, antibodies or antibody fragments adapted from naturally occurring antibodies, antibodies constructed de novo using sequences of antibodies or antibody fragments known to be specific for an antigen of interest. Sequences that can be derived from parental antibodies include heavy and/or light chain variable regions and/or CDRs, framework regions or other portions thereof.

In some embodiments, the bispecific antibody can be subjected to an alteration to render it less immunogenic when administered to a human. Such an alteration can comprise one or more of the techniques commonly known as chimerization, humanization, CDR-grafting, deimmunization and/or mutation of framework region amino acids to correspond to the closest human germline sequence (germlining). Bispecific antibodies which have been altered will therefore remain administrable for a longer period of time with reduced or no immune response-related side effects than corresponding bispecific antibodies which have not undergone any such alteration(s), One of ordinary skill in the art will understand how to determine whether, and to what degree an antibody must be altered in order to prevent it from eliciting an unwanted host immune response.

As used herein, a "killer cell" may be a cytotoxic T cells, a gamma-delta T cells, a natural killer (NK) cells, and natural killer T (NKT) cells.

Generally a linker has no specific biological activity other than to join the proteins or to preserve some minimum distance or other spatial relationship between them. However, the constituent amino acids of a linker can be selected to influence some property of the molecule such as the folding, net charge, or hydrophobicity of the molecule. Peptide linkers (-) suitable for production of scFv antibodies are described in Kumada Y, et al. Biochemical Engineering Journal. 2007 35 (2):158-165; Albrecht H, et al. J Immunol Methods. 2006 310 (1-2):100-16; Feng J, et al. J Immunol Methods. 2003 282 (1-2):33-43; Griffiths A D, et al. Curr Opin Biotechnol. 1998 9 (1):102-8; Huston J S, et al. Methods Enzymol. 1991 203:46-88; Bird R E, et al. Science. 1988 242 (4877):423-6; Takkinen K, et al. Protein Eng. 1991 4 (7):837-41; Smallshaw J E, et al. Protein Eng. 1999 12 (7):623-30; Argos P. J Mol Biol. 1990 211 (4):943-58; and Whitlow M, et al. Protein Eng. 1993 6 (8):989-95, which are hereby incorporated by reference for the teachings of these linkers and methods of producing scFv antibodies against different targets using various linkers.

The particular length of the peptide linker used to join the scFv molecules together is important in determining half-life, immunogenicity, and activity of the overall construct. In some embodiments, the linker sequence is 4, 5, 6, 7, 8, 9, 10, 11, 12, 13, 14, 15, 16, 17, 18, 19, 20, 21, 22, 23, 24, 25 or more amino acids in length. In some embodiments, the linker sequence (-) comprises a fragment of the human muscle aldose protein, (SEQ ID NO: 10), or a variant thereof. The linker is preferably long enough to not interfere with proper folding and association of the V$_H$-V$_L$ chains but not so long as to cause added immunogenicity.

The protein or fragment disclosed herein can also include at least one additional linker for linking the V$_H$ and the V$_L$ chains of a single scFv. For example, the linker may be a glycine-serine linker that can be varied in sizes from 3-5 repeats of GGGGS (SEQ ID NO:22). For example, SEQ ID NO:8 is 3 repeats of GGGGS (SEQ ID NO:22) to yield a 15 amino acid long linker. Other potential sequences for linking the V$_H$ and the V$_L$ chains of a single scFv include artificial linkers containing the first six amino acids of the CHI domain, and/or the hydrophilic alpha-tubulin peptide sequence.

Also disclosed is a polynucleotide encoding a polypeptide disclosed herein. Also disclosed is a vector comprising the disclosed polynucleotide. A vector is a nucleic acid molecule used as a vehicle to transfer (foreign) genetic material into a cell. The term "vector" encompasses—but is not restricted to—plasmids, viruses, cosmids and artificial chromosomes. In general, engineered vectors comprise an origin of replication, a multicloning site and a selectable marker. The vector itself is generally a nucleotide sequence, commonly a DNA sequence, that comprises an insert (transgene) and a larger sequence that serves as the "backbone" of the vector. Modern vectors may encompass additional features besides the transgene insert and a backbone: promoter, genetic marker, antibiotic resistance, reporter gene, targeting sequence, protein purification tag. Expression vectors are for the expression of the transgene in the target cell, and generally have control sequences. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Also disclosed is a host cell transformed or transfected with the disclosed polynucleotide or vector. As used herein, the terms "host cell" or "recipient cell" are intended to include any individual cell or cell culture that can be or has/have been recipients of vectors, exogenous nucleic acid molecules, and polynucleotides encoding the disclosed polypeptide; and/or recipients of the polypeptide itself. The introduction of the respective material into the cell is carried out by way of transformation, transfection and the like. The term "host cell" is also intended to include progeny or potential progeny of a single cell. Because certain modifications may occur in succeeding generations due to either natural, accidental, or deliberate mutation or due to environmental influences, such progeny may not, in fact, be completely identical (in morphology or in genomic or total DNA complement) to the parent cell, but is still included within the scope of the term as used herein. Suitable host cells include prokaryotic or eukaryotic cells, and also include but are not limited to bacteria, yeast cells, fungi cells, plant cells, and animal cells such as insect cells and mammalian cells, e.g., murine, rat, macaque or human.

The disclosed polypeptide can be produced in bacteria. In addition to prokaryotes, eukaryotic microbes such as filamentous fungi or yeast are suitable cloning or expression hosts for the disclosed polypeptide. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe, Kluyveromyces* hosts such *as K. lactis, K. fragilis* (ATCC 12424), *K. bulgaricus* (ATCC 16045), *K. wickeramii* (ATCC 24178), *K. waltii* (ATCC 56500), *K. drosophilarum* (ATCC 36906), *K. thermotolerans*, and *K. marxiamus; yarrowia* (EP 402 226); *Pichia pastoris* (EP 183 070); *Candida; Trichoderma reesia* (EP 244 234); *Neurospora crassa; Schwanniomyces* such as *Schwanniomyces occidentalis*; and filamentous fungi such as *Neurospora, Penicillium, Tolypocladium* and *Aspergillus* hosts such as *A. nidulans* and *A. niger*.

Suitable host cells for the expression of glycosylated polypeptides are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruit fly), and *Bombyx mori* have been identified. A variety of viral strains for transfection are publicly available, e.g., the L-1 variant of *Autographa californica* NPV and the Bm-5 strain of *Bombyx mori* NPV Plant cell cultures of cotton, corn, potato, soybean, petunia, tomato, Arabidopsis and tobacco can also be used as hosts. Cloning and expression vectors useful in the production of proteins in plant cell culture are known to those of skill in the art.

Suitable host cells also include vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36: 59 (1977)); baby hamster kidney cells (BHK, ATCC CCL 10); Chinese hamster ovary cells/-DHFR (CHO, Urlaub of al., Proc. Natl. Acad. Sci. USA 77: 4216 (1980)); mouse Sertoli cells (TM4, Mather, Biol. Reprod. 23: 243-251 (1980)); monkey kidney cells (CV1 ATCC CCL 70); African green monkey kidney cells (VERO-76, ATCC CRL1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2,1413 8065); mouse mammary tumor (MMT 060562, ATCC CCL5 1); TR1 cells (Mather et al., Annals N. Y Acad. Sci. (1982) 383: 44-68); MRC 5 cells; FS4 cells; and a human hepatoma line (Hep G2).

Also disclosed is a process for the production of a polypeptide disclosed herein, said process comprising culturing a host cell disclosed herein under conditions allowing the expression of the disclosed polypeptide and recovering the polypeptide from the culture.

When using recombinant techniques, the disclosed polypeptide can be produced intracellularly, in the periplasmic space, or directly secreted into the medium. If the polypeptide is produced intracellularly, as a first step, the particulate debris, either host cells or lysed fragments, are removed, for example, by centrifugation or ultrafiltration. Polypeptides can also be secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the polypeptide is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The disclosed polypeptide prepared from the host cells can be recovered or purified using, for example, hydroxylapatite chromatography, gel electrophoresis, dialysis, and affinity chromatography. Other techniques for protein purification such as fractionation on an ion-exchange column, ethanol precipitation, Reverse Phase HPLC, chromatography on silica, chromatography on heparin SEPHAROSE™, chromatography on an anion or cation exchange resin (such as a polyaspartic acid column), chromato-focusing, SDS-PAGE, and ammonium sulfate precipitation are also available depending on the polypeptide to be recovered. Where the disclosed polypeptide comprises a CH3 domain, the Bakerbond ABX resin (J. T. Baker, Phillipsburg, N.J.) is useful for purification.

Affinity chromatography can be used. The matrix to which the affinity ligand is attached is most often agarose, but other matrices are available. Mechanically stable matrices such as controlled pore glass or poly (styrenedivinyl) benzene allow for faster flow rates and shorter processing times than can be achieved with agarose.

Also disclosed is a pharmaceutical composition comprising a polypeptide disclosed herein in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compounds described herein can be formulated for parenteral administration. Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof.

The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine.

Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monola.urate, polysorbates, polyoxyethylene octylphenylether, PEG-1000 cetyl ether, polyoxyethylene tridecyl ether, polypropylene glycol butyl ether, POLOXAMER® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

Peptides may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. For example, PEGylation is a preferred chemical modification for pharmaceutical usage. Other moieties that may be used include: propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane.

For oral formulations, the location of release may be the stomach, the small intestine (the duodenum, the jejunem, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the peptide (or derivative) or by release of the peptide (or derivative) beyond the stomach environment, such as in the intestine.

To ensure full gastric resistance a coating can be impermeable to at least pH 5.0. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (i.e. powder), for liquid forms a soft gelatin shell may be used. The shell material of cachets could be thick starch or other edible paper. For pills, lozenges, molded tablets or tablet triturates, moist massing techniques can be used.

To aid dissolution of peptides into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 20, 40, 60, 65 and 80, sucrose fatty acid ester, methyl cellulose and carboxymethyl cellulose. These surfactants could be present in the formulation of the protein or derivative either alone or as a mixture in different ratios.

Additives which potentially enhance uptake of peptides are for instance the fatty acids oleic acid, linoleic acid and linolenic acid.

Controlled release oral formulations may be desirable. The peptides could be incorporated into an inert matrix which permits release by either diffusion or leaching mechanisms, e.g., gums. Slowly degenerating matrices may also be incorporated into the formulation. Some enteric coatings also have a delayed release effect. Another form of a controlled release is by a method based on the Oros therapeutic system (Alza Corp.), i.e. the drug is enclosed in a semipermeable membrane which allows water to enter and push drug out through a single small opening due to osmotic effects.

Other coatings may be used for the formulation. These include a variety of sugars which could be applied in a coating pan. The peptides could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols. The second group consists of the enteric materials that are commonly esters of phthalic acid.

A mix of materials might be used to provide the optimum film coating. Film coating may be carried out in a pan coater or in a fluidized bed or by compression coating.

Also disclosed is a method for treating cancers in a subject in need thereof that involves administering a polypeptide disclosed herein to the subject. In some cases, the polypeptide is administered in a therapeutically effective amount.

The herein disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, intracavity, or transdermally. The compositions may be administered orally, parenterally (e.g., intravenously), by intramuscular injection, by intraperitoneal injection, transdermally, extracorporeally, ophthalmically, vaginally, rectally, intranasally, topically or the like, including topical intranasal administration or administration by inhalant.

Parenteral administration of the composition, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

The compositions disclosed herein may be administered prophylactically to patients or subjects who are at risk for cancer. Thus, the method can further comprise identifying a subject at risk for cancer prior to administration of the herein disclosed compositions.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, N.Y. (1977) pp. 365-389. A typical daily dosage of the antibody used alone might range from about 1 µg/kg to up to 100 mg/kg of body weight or more per day, depending on the factors mentioned above.

In some embodiments, the disclosed polypeptide is administered in a dose equivalent to parenteral administration of about 0.1 ng to about 100 g per kg of body weight, about 10 ng to about 50 g per kg of body weight, about 100 ng to about 1 g per kg of body weight, from about 1 µg to about 100 mg per kg of body weight, from about 1 µg to about 50 mg per kg of body weight, from about 1 mg to about 500 mg per kg of body weight; and from about 1 mg to about 50 mg per kg of body weight. Alternatively, the amount of polypeptide administered to achieve a therapeutic effective dose is about 0.1 ng, 1 ng, 10 ng, 100 ng, 1 µg, 10 µg, 100 µg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The cancer of the disclosed methods can be any cell in a subject undergoing unregulated growth, invasion, or metastasis. In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

A number of embodiments of the invention have been described. Nevertheless, it will be understood that various modifications can be made without departing from the spirit and scope of the invention. Accordingly, other embodiments are within the scope of the following claims.

EXAMPLES

Example 1: Production of Anti-CS-1 TriCLE and its Characteristics

Materials and Methods

Cloning of anti-CS1 and anti-EGFRvIII TriCLE. TriCLE was designed in silco and synthesized as a gene fragment (Invitrogen). The gene fragment was cloned into an expression vector (e.g. pGEX6p-1 and pET21d). SEC ID NOs:1 and 2 provide the nucleotide sequences for the pET21d-TriCLE and pGEX6p-1-TriCLE, respectively.

Protein production. The expression of the protein was induced by the addition of 100 µM IPTG for overnight at 30° C. The bacterial cells were then harvested and lysed by sonication in lysis buffer containing Tris pH7.4 and protease inhibitors. The TriCLE protein was purified in HisTRAP column (GE Health Science), refolded and dialysed with PBS/glycerin using centrifugation filter units. The concentration of the TriCLE was measured and diluted for experiments.

Flow cytometry. The binding affinity of the TriCLE was tested by using flow cytometry, $2 \times 10^{-5}$ of the multiple myeloma cell line (e.g. MM1.s) or a glioblastoma (GBM) cell line was used to stain with the TriCLE as primary staining reagent and then biotin-labelled protein L was used to detect the presence of scFv and detected by PE conjugated anti-biotin antibody by flow cytometry. For other phenotyping on human peripheral blood mononuclear cells, these antibodies were used: CD56-APC (Beckman Coulter), CD3-APCH7 (BD Bioscience), CD14-FITC (BD Bioscience), CD69-PE (Beckman Coulter).

Cytotoxicity assay. The cytotoxicity assay for the TriCLE was performed for 24 and 48 h. Therefore, a flow-based cytotoxicity assay was used. Briefly, the NK cell line NKL was mixed with the multiple myeloma cell line H929 cells at effector-to-target ratio of 20:1. TriCLE was added to the coculture at the indicated increasing dose from 50 pg/mL to 10 ug/mL and incubated for 2 hours. NKL alone and H929 alone with or without TriCLE were used as controls to determine the toxicity of the TriCLE. The cells were harvested and analyzed by flow cytometry to determine the percentage of live and dead cells for each condition.

Sequences:
DNA sequence of pET21d- anti-CS-1-TriCLE
(SEQ ID NO: 1)
ATCCGGATATAGTTCCTCCTTTCAGCAAAAAACCCCTCAAGACCCGTTTA

GAGGCCCCAAGGGGTTATGCTAGTTATTGCTCAGCGGTGGCAGCAGCCAA

CTCAGCTTCCTTTCGGGCTTTGTTAGCAGCCGGATCTCAGCGGCCGCGTG

GTGATGATGGTGATGGCTCTGTACCTGCAGCTGCTGCGGACCCGCCTCAA

GAACGCGCGGGCCGGCTGATACCTTCAGGGAACATTTGGCCGAACCATAG

CTGAAGGTGGTGTACCACATGTTCCACACTTTCTGGCGGGGCCCTGGCC

CAGTTCCCAGATGCCCATGATATGTGGGCTATCGCTTTCGGTGCGCAGAT

TCTGTTTAAATTTGTCTTTCGCAGTCAGAGTCACGTCTTTTGAAGAGGAG

GTGGCATACATTTGCAGAGAGGAAGGGGTCGACTCATCGCTGGCCACGTA

ATAGCACGCCCGCGATGTCATAATCGCGGTCCGTGCCATATCGTACCATC

CTTGGCCCGTCGACACCGTCACGGAGCCCCCTCCCCCGCTGCCCCCACCG

CCACTACCACCGCCGCCAGAGTCAATCACCATGGTTTGGGACTGCTTGCT

CATGGAGGTGCTAACTCCGTCGCGAACTGAAATTGTACATTTGGCAGACT

GGTCCACGATCGTTCCCACCGCCCAGTACTGCTGTTTCGGACCCTGAGAA

GGTTTCAGAAGGATATAGCTTGCACTATACCGGTACGTACCTACCGGATC

ACGGAACGTACCGCTGCCTGATCCTGTATCAAAGGTAAAGGTAATAGAGT

TCACCTGCGCTTCGTCAAGCGCCACGTAATAGCACTGCTGGTGATAGCTC

GTAGGGAGGGTAAATCCCGCACCCGTCTTGAGTTCCAGTTTGTAGGCGTG

ATTTGACACAAACAGGGACTCCGATGCCGCCGCGCCCGCCTGGCCGCTCG

GCAGCACGGTCAGTTTAGTACCGCCGCCAAAAACTGGGCCATTTAAGCTA

TCATCCCATGCGGCGCAATAATAATCAGCTTCATCCTCGCTCTGGAGACC

CGAAATAGCCAGAAAAGCCGAGGTACCCGATTTACTGCCGGAAAAGCGGT

CACTAACTCCACTTGGCAGCAAATCATCATAGTAAATCAGCAGTTTCGGC

GCTTTTCCCGGCAGTTGCTGATACCAGTTCACTGCGTTGTTACCGATGTT

GGAGCTGCTCCCACTACAGCTGATCGTGATCGACTGACCCGGGGAACCCG

ACACCGACGCCGGCTGCGTAAGCGCTGACTGACTGCCACCTCCGCCGCTG
CCACCGCCACCAGAGCCGCCCCCACCTGAACTAACGGTAACGGTGGTGCC
CTGACCCCAGTAATCGAAGTACGTACCATCACCCAGGCCACGATCTTTAG
CGCAATAGTAAACGGCGGTATCTTCGGCGCGCAGGCTATTCATTTGCAGG
TACAGGGTATTTTTGCTATTGTCGCGGCTAATAGTGAAGCGTCCTTTTAC
TGAGTCGGCATAATATTTGTTAGACCCATCGTAGCGGATGAACGCAACCC
ACTCCAGACCTTTGCCAGGCGCCTGACGCACCCAATGCATACCATAAGAG
CTGAAGGTAAAACCCGACGCGGCACAGCTCAGACGCAAAGAGCCGCCCGG
CTTGACCAGACCGCCACCGGATTCAACCAGCTGCACTTGCATGAATTCTA
TATCTCCTTCTTAAAGTTAAACAAAATTATTTCTAGAGGGGAATTGTTAT
CCGCTCACAATTCCCCTATAGTGAGTCGTATTAATTTCGCGGGATCGAGA
TCTCGATCCTCTACGCCGGACGCATCGTGGCCGGCATCACCGGCGCCACA
GGTGCGGTTGCTGGCGCCTATATCGCCGACATCACCGATGGGGAAGATCG
GGCTCGCCACTTCGGGCTCATGAGCGCTTGTTTCGGCGTGGGTATGGTGG
CAGGCCCCGTGGCCGGGGACTGTTGGGCGCCATCTCCTTGCATGCACCA
TTCCTTGCGGCGGCGGTGCTCAACGGCCTCAACCTACTACTGGGCTGCTT
CCTAATGCAGGAGTCGCATAAGGGAGAGCGTCGAGATCCCGGACACCATC
GAATGGCGCAAAACCTTTCGCGGTATGGCATGATAGCGCCCGGAAGAGAG
TCAATTCAGGGTGGTGAATGTGAAACCAGTAACGTTATACGATGTCGCAG
AGTATGCCGGTGTCTCTTATCAGACCGTTTCCCGCGTGGTGAACCAGGCC
AGCCACGTTTCTGCGAAAACGCGGGAAAAAGTGGAAGCGGCGATGGCGGA
GCTGAATTACATTCCCAACCGCGTGGCACAACAACTGGCGGGCAAACAGT
CGTTGCTGATTGGCGTTGCCACCTCCAGTCTGGCCCTGCACGCGCCGTCG
CAAATTGTCGCGGCGATTAAATCTCGCGCCGATCAACTGGGTGCCAGCGT
GGTGGTGTCGATGGTAGAACGAAGCGGCGTCGAAGCCTGTAAAGCGGCGG
TGCACAATCTTCTCGCGCAACGCGTCAGTGGGCTGATCATTAACTATCCG
CTGGATGACCAGGATGCCATTGCTGTGGAAGCTGCCTGCACTAATGTTCC
GGCGTTATTTCTTGATGTCTCTGACCAGACACCCATCAACAGTATTATTT
TCTCCCATGAAGACGGTACGCGACTGGGCGTGGAGCATCTGGTCGCATTG
GGTCACCAGCAAATCGCGCTGTTAGCGGGCCCATTAAGTTCTGTCTCGGC
GCGTCTGCGTCTGGCTGGCTGGCATAAATATCTCACTCGCAATCAAATTC
AGCCGATAGCGGAACGGGAAGGCGACTGGAGTGCCATGTCCGGTTTTCAA
CAAACCATGCAAATGCTGAATGAGGGCATCGTTCCCACTGCGATGCTGGT
TGCCAACGATCAGATGGCGCTGGGCGCAATGCGCGCCATTACCGAGTCCG
GGCTGCGCGTTGGTGCGGATATCTCGGTAGTGGGATACGACGATACCGAA
GACAGCTCATGTTATATCCCGCCGTTAACCACCATCAAACAGGATTTTCG
CCTGCTGGGGCAAACCAGCGTGGACCGCTTGCTGCAACTCTCTCAGGGCC
AGGCGGTGAAGGGCAATCAGCTGTTGCCCGTCTCACTGGTGAAAAGAAAA
ACCACCCTGGCGCCCAATACGCAAACCGCCTCTCCCCGCGCGTTGGCCGA
TTCATTAATGCAGCTGGCACGACAGGTTTCCCGACTGGAAAGCGGGCAGT

GAGCGCAACGCAATTAATGTAAGTTAGCTCACTCATTAGGCACCGGGATC
TCGACCGATGCCCTTGAGAGCCTTCAACCCAGTCAGCTCCTTCCGGTGGG
CGCGGGGCATGACTATCGTCGCCGCACTTATGACTGTCTTCTTTATCATG
CAACTCGTAGGACAGGTGCCGGCAGCGCTCTGGGTCATTTTCGGCGAGGA
CCGCTTTCGCTGGAGCGCGACGATGATCGGCCTGTCGCTTGCGGTATTCG
GAATCTTGCACGCCCTCGCTCAAGCCTTCGTCACTGGTCCCGCCACCAAA
CGTTTCGGCGAGAAGCAGGCCATTATCGCCGGCATGGCGGCCCCACGGGT
GCGCATGATCGTGCTCCTGTCGTTGAGGACCCGGCTAGGCTGGCGGGGTT
GCCTTACTGGTTAGCAGAATGAATCACCGATACGCGAGCGAACGTGAAGC
GACTGCTGCTGCAAAACGTCTGCGACCTGAGCAACAACATGAATGGTCTT
CGGTTTCCGTGTTTCGTAAAGTCTGGAAACGCGGAAGTCAGCGCCCTGCA
CCATTATGTTCCGGATCTGCATCGCAGGATGCTGCTGGCTACCCTGTGGA
ACACCTACATCTGTATTAACGAAGCGCTGGCATTGACCCTGAGTGATTTT
TCTCTGGTCCCGCCGCATCCATACCGCCAGTTGTTTACCCTCACAACGTT
CCAGTAACCGGGCATGTTCATCATCAGTAACCCGTATCGTGAGCATCCTC
TCTCGTTTCATCGGTATCATTACCCCCATGAACAGAAATCCCCCTTACAC
GGAGGCATCAGTGACCAAACAGGAAAAAACCGCCCTTAACATGGCCCGCT
TTATCAGAAGCCAGACATTAACGCTTCTGGAGAAACTCAACGAGCTGGAC
GCGGATGAACAGGCAGACATCTGTGAATCGCTTCACGACCACGCTGATGA
GCTTTACCGCAGCTGCCTCGCGCGTTTCGGTGATGACGGTGAAAACCTCT
GACACATGCAGCTCCCGGAGACGGTCACAGCTTGTCTGTAAGCGGATGCC
GGGAGCAGACAAGCCCGTCAGGGCGCGTCAGCGGGTGTTGGCGGGTGTCG
GGGCGCAGCCATGACCCAGTCACGTAGCGATAGCGGAGTGTATACTGGCT
TAACTATGCGGCATCAGAGCAGATTGTACTGAGAGTGCACCATATATGCG
GTGTGAAATACCGCACAGATGCGTAAGGAGAAAATACCGCATCAGGCGCT
CTTCCGCTTCCTCGCTCACTGACTCGCTGCGCTCGGTCGTTCGGCTGCGG
CGAGCGGTATCAGCTCACTCAAAGGCGGTAATACGGTTATCCACAGAATC
AGGGGATAACGCAGGAAAGAACATGTGAGCAAAAGGCCAGCAAAAGGCCA
GGAACCGTAAAAAGGCCGCGTTGCTGGCGTTTTTCCATAGGCTCCGCCCC
CCTGACGAGCATCACAAAAATCGACGCTCAAGTCAGAGGTGGCGAAACCC
GACAGGACTATAAAGATACCAGGCGTTTCCCCCTGGAAGCTCCCTCGTGC
GCTCTCCTGTTCCGACCCTGCCGCTTACCGGATACCTGTCCGCCTTTCTC
CCTTCGGGAAGCGTGGCGCTTTCTCATAGCTCACGCTGTAGGTATCTCAG
TTCGGTGTAGGTCGTTCGCTCCAAGCTGGGCTGTGTGCACGAACCCCCCG
TTCAGCCCGACCGCTGCGCCTTATCCGGTAACTATCGTCTTGAGTCCAAC
CCGGTAAGACACGACTTATCGCCACTGGCAGCAGCCACTGGTAACAGGAT
TAGCAGAGCGAGGTATGTAGGCGGTGCTACAGAGTTCTTGAAGTGGTGGC
CTAACTACGGCTACACTAGAAGGACAGTATTTGGTATCTGCGCTCTGCTG
AAGCCAGTTACCTTCGGAAAAAGAGTTGGTAGCTCTTGATCCGGCAAACA
AACCACCGCTGGTAGCGGTGGTTTTTTTGTTTGCAAGCAGCAGATTACGC
GCAGAAAAAAAGGATCTCAAGAAGATCCTTTGATCTTTTCTACGGGGTCT

-continued

GACGCTCAGTGGAACGAAAACTGACGTTAAGGGATTTTGGTCATGAGATT

ATCAAAAAGGATCTTCACCTAGATCCTTTTAAATTAAAAATGAAGTTTTA

AATCAATCTAAAGTATATATGAGTAAACTTGGTCTGACAGTTACCAATGC

TTAATCAGTGAGGCACCTATCTCAGCGATCTGTCTATTTCGTTCATCCAT

AGTTGCCTGACTCCCCGTCGTGTAGATAACTACGATACGGGAGGGCTTAC

CATCTGGCCCCAGTGCTGCAATGATACCGCGAGACCCACGCTCACCGGCT

CCAGATTTATCAGCAATAAACCAGCCAGCCGGAAGGGCCGAGCGCAGAAG

TGGTCCTGCAACTTTATCCGCCTCCATCCAGTCTATTAATTGTTGCCGGG

AAGCTAGAGTAAGTAGTTCGCCAGTTAATAGTTTGCGCAACGTTGTTGCC

ATTGCTGCAGGCATCGTGGTGTCACGCTCGTCGTTTGGTATGGCTTCATT

CAGCTCCGGTTCCCAACGATCAAGGCGAGTTACATGATCCCCCATGTTGT

GCAAAAAAGCGGTTAGCTCCTTCGGTCCTCCGATCGTTGTCAGAAGTAAG

TTGGCCGCAGTGTTATCACTCATGGTTATGGCAGCACTGCATAATTCTCT

TACTGTCATGCCATCCGTAAGATGCTTTTCTGTGACTGGTGAGTACTCAA

CCAAGTCATTCTGAGAATAGTGTATGCGGCGACCGAGTTGCTCTTGCCCG

GCGTCAATACGGGATAATACCGCGCCACATAGCAGAACTTTAAAAGTGCT

CATCATTGGAAAACGTTCTTCGGGGCGAAAACTCTCAAGGATCTTACCGC

TGTTGAGATCCAGTTCGATGTAACCCACTCGTGCACCCAACTGATCTTCA

GCATCTTTTACTTTGACCAGCGTTTCTGGGTGAGCAAAAACAGGAAGGCA

AAATGCCGCAAAAAAGGGAATAAGGGCGACACGGAAATGTTGAATACTCA

TACTCTTCCTTTTTCAATATTATTGAAGCATTTATCAGGGTTATTGTCTC

ATGAGCGGATACATATTTGAATGTATTTAGAAAAATAAACAAATAGGGGT

TCCGCGCACATTTCCCCGAAAAGTGCCACCTGAAATTGTAAACGTTAATA

TTTTGTTAAAATTCGCGTTAAATTTTTGTTAAATCAGCTCATTTTTTAAC

CAATAGGCCGAAATCGGCAAAATCCCTTATAAATCAAAAGAATAGACCGA

GATAGGGTTGAGTGTTGTTCCAGTTTGGAACAAGAGTCCACTATTAAAGA

ACGTGGACTCCAACGTCAAAGGGCGAAAAACCGTCTATCAGGGCGATGGC

CCACTACGTGAACCATCACCCTAATCAAGTTTTTTGGGGTCGAGGTGCCG

TAAAGCACTAAATCGGAACCCTAAAGGGAGCCCCCGATTTAGAGCTTGAC

GGGGAAAGCCGGCGAACGTGGCGAGAAAGGAAGGGAAGAAAGCGAAAGGA

GCGGGCGCTAGGGCGCTGGCAAGTGTAGCGGTCACGCTGCGCGTAACCAC

CACACCCGCCGCGCTTAATGCGCCGCTACAGGCGCGTCCCATTCGCCA

DNA sequence of pGEX6p1m-anti-CS-1-TriCLE (SEQ ID NO: 2)

ACGTTATCGACTGCACGGTGCACCAATGCTTCTGGCGTCAGGCAGCCATC

GGAAGCTGTGGTATGGCTGTGCAGGTCGTAAATCACTGCATAATTCGTGT

CGCTCAAGGCGCACTCCCGTTCTGGATAATGTTTTTTGCGCCGACATCAT

AACGGTTCTGGCAAATATTCTGAAATGAGCTGTTGACAATTAATCATCGG

CTCGTATAATGTGTGGAATTGTGAGCGGATAACAATTTCACACAGGAAAC

AGTATTCGGATCCCCGGAATTCATGCAAGTGCAGCTGGTTGAATCCGGTG

GCGGTCTGGTCAAGCCGGGCGGCTCTTTGCGTCTGAGCTGTGCCGCGTCG

GGTTTTACCTTCAGCTCTTATGGTATGCATTGGGTGCGTCAGGCGCCTGG

CAAAGGTCTGGAGTGGGTTGCGTTCATCCGCTACGATGGGTCTAACAAAT

ATTATGCCGACTCAGTAAAAGGACGCTTCACTATTAGCCGCGACAATAGC

AAAAATACCCTGTACCTGCAAATGAATAGCCTGCGCGCCGAAGATACCGC

CGTTTACTATTGCGCTAAAGATCGTGGCCTGGGTGATGGTACGTACTTCG

ATTACTGGGGTCAGGGCACCACCGTTACCGTTAGTTCAGGTGGGGGCGGC

TCTGGTGGCGGTGGCAGCGGCGGAGGTGGCAGTCAGTCAGCGCTTACGCA

GCCGGCCGTCGGTGTCGGGTTCCCCGGGTCAGTCGATCACGATCAGCTGTA

GTGGGAGCAGCTCCAACATCGGTAACAACGCAGTGAACTGGTATCAGCAA

CTGCCGGGAAAAGCGCCGAAACTGCTGATTTACTATGATGATTTGCTGCC

AAGTGGAGTTAGTGACCGCTTTTCCGGCAGTAAATCGGGTACCTCGGCTT

TTCTGGCTATTTCGGGTCTCCAGAGCGAGGATGAAGCTGATTATTATTGC

GCCGCATGGGATGATAGCTTAAATGGCCCAGTTTTTGGCGGCGGTACTAA

ACTGACCGTGCTGCCGAGCGGCCAGGCGGGCGCGGCGGCATCGGAGTCCC

TGTTTGTGTCAAATCACGCCTACAAACTGGAACTCAAGACGGGTGCGGGA

TTTACCCTCCCTACGAGCTATCACCAGCAGTGCTATTACGTGGCGCTTGA

CGAAGCGCAGGTGAACTCTATTACCTTTACCTTTGATACAGGATCAGGCA

GCGGTACGTTCCGTGATCCGGTAGGTACGTACCGGTATAGTGCAAGCTAT

ATCCTTCTGAAACCTTCTCAGGGTCCGAAACAGCAGTACTGGGCGGTGGG

AACGATCGTGGACCAGTCTGCCAAATGTACAATTTCAGTTCGCGACGGAG

TTAGCACCTCCATGAGCAAGCAGTCCCAAACCATGGTGATTGACTCTGGC

GGCGGTGGTAGTGGCGGTGGGGGCAGCGGGGAGGGGCTCCGTGACGGT

GTCGACGGGCCAAGGATGGTACGATATGGCACGGACCGCGATTATGACAT

CGCGGGCGTGCTATTACGTGGCCAGCGATGAGTCGACCCCTTCCTCTCTG

CAAATGTATGCCACCTCCTCTTCAAAAGACGTGACTCTGACTGCGAAAGA

CAAATTTAAACAGAATCTGCGCACCGAAAGCGATAGCCCACATATCATGG

GCATCTGGGAACTGGGCCAGGCCCCCGCCAGAAAGTGTGGAACATGTGG

TACACCACCTTCAGCTATGGTTCGGCCAAATGTTCCCTGAAGGTATCAGC

CGGCCCGCGCGTTCTTGAGGCGGGTCCGCAGCAGCTGCAGGTACAGAGCC

ATCACCATCATCACCACGCGGCCGCATCGTGACTGACTGACGATCTGCCT

CGCGCGTTTCGGTGATGACGGTGAAAACCTCTGACACATGCAGCTCCCGG

AGACGGTCACAGCTTGTCTGTAAGCGGATGCCGGGAGCAGACAAGCCCGT

CAGGGCGCGTCAGCGGGTGTTGGCGGGTGTCGGGGCGCAGCCATGACCCA

GTCACGTAGCGATAGCGGAGTGTATAATTCTTGAAGACGAAAGGGCCTCG

TGATACGCCTATTTTTATAGGTTAATGTCATGATAATAATGGTTTCTTAG

ACGTCAGGTGGCACTTTTCGGGGAAATGTGCGCGGAACCCCTATTTGTTT

ATTTTTCTAAATACATTCAAATATGTATCCGCTCATGAGACAATAACCCT

GATAAATGCTTCAATAATATTGAAAAAGGAAGAGTATGAGTATTCAACAT

TTCCGTGTCGCCCTTATTCCCTTTTTTGCGGCATTTTGCCTTCCTGTTTT

TGCTCACCCAGAAACGCTGGTGAAAGTAAAAGATGCTGAAGATCAGTTGG

GTGCACGAGTGGGTTACATCGAACTGGATCTCAACAGCGGTAAGATCCTT

-continued

```
GAGAGTTTTCGCCCCGAAGAACGTTTTCCAATGATGAGCACTTTTAAAGT
TCTGCTATGTGGCGCGGTATTATCCCGTGTTGACGCCGGGCAAGAGCAAC
TCGGTCGCCGCATACACTATTCTCAGAATGACTTGGTTGAGTACTCACCA
GTCACAGAAAAGCATCTTACGGATGGCATGACAGTAAGAGAATTATGCAG
TGCTGCCATAACCATGAGTGATAACACTGCGGCCAACTTACTTCTGACAA
CGATCGGAGGACCGAAGGAGCTAACCGCTTTTTTGCACAACATGGGGGAT
CATGTAACTCGCCTTGATCGTTGGGAACCGGAGCTGAATGAAGCCATACC
AAACGACGAGCGTGACACCACGATGCCTGCAGCAATGGCAACAACGTTGC
GCAAACTATTAACTGGCGAACTACTTACTCTAGCTTCCCGGCAACAATTA
ATAGACTGGATGGAGGCGGATAAAGTTGCAGGACCACTTCTGCGCTCGGC
CCTTCCGGCTGGCTGGTTTATTGCTGATAAATCTGGAGCCGGTGAGCGTG
GGTCTCGCGGTATCATTGCAGCACTGGGGCCAGATGGTAAGCCCTCCCGT
ATCGTAGTTATCTACACGACGGGGAGTCAGGCCAACTATGGATGAACGAA
ATAGACAGATCGCTGAGATAGGTGCCTCACTGATTAAGCATTGGTAACTG
TCAGACCAAGTTTACTCATATATACTTTAGATTGATTTAAAACTTCATTT
TTAATTTAAAAGGATCTAGGTGAAGATCCTTTTTTGATAATCTCATGACCA
AAATCCCTTAACGTGAGTTTTCGTTCCACTGAGCGTCAGACCCCGTAGAA
AAGATCAAAGGATCTTCTTGAGATCCTTTTTTTCTGCGCGTAATCTGCTG
CTTGCAAACAAAAAAACCACCGCTACCAGCGGTGGTTTGTTTGCCGGATC
AAGAGCTACCAACTCTTTTTCCGAAGGTAACTGGCTTCAGCAGAGCGCAG
ATACCAAATACTGTCCTTCTAGTGTAGCCGTAGTTAGGCCACCACTTCAA
GAACTCTGTAGCACCGCCTACATACCTCGCTCTGCTAATCCTGTTACCAG
TGGCTGCTGCCAGTGGCGATAAGTCGTGTCTTACCGGGTTGGACTCAAGA
CGATAGTTACCGGATAAGGCGCAGCGGTCGGGCTGAACGGGGGGTTCGTG
CACACAGCCCAGCTTGGAGCGAACGACCTACACCGAACTGAGATACCTAC
AGCGTGAGCTATGAGAAAGCGCCACGCTTCCCGAAGGGAGAAAGGCGGAC
AGGTATCCGGTAAGCGGCAGGGTCGGAACAGGAGAGCGCACGAGGGAGCT
TCCAGGGGGAAACGCCTGGTATCTTTATAGTCCTGTCGGGTTTCGCCACC
TCTGACTTGAGCGTCGATTTTTGTGATGCTCGTCAGGGGGCGGAGCCTA
TGGAAAAACGCCAGCAACGCGGCCTTTTTACGGTTCCTGGCCTTTTGCTG
GCCTTTTGCTCACATGTTCTTTCCTGCGTTATCCCCTGATTCTGTGGATA
ACCGTATTACCGCCTTTGAGTGAGCTGATACCGCTCGCCGCAGCCGAACG
ACCGAGCGCAGCGAGTCAGTGAGCGAGGAAGCGGAAGAGCGCCTGATGCG
GTATTTTCTCCTTACGCATCTGTGCGGTATTTCACACCGCATAAATTCCG
ACACCATCGAATGGTGCAAAACCTTTCGCGGTATGGCATGATAGCGCCCG
GAAGAGAGTCAATTCAGGGTGGTGAATGTGAAACCAGTAACGTTATACGA
TGTCGCAGAGTATGCCGGTGTCTCTTATCAGACCGTTTCCCGCGTGGTGA
ACCAGGCCAGCCACGTTTCTGCGAAAACGCGGGAAAAAGTGGAAGCGGCG
ATGGCGGAGCTGAATTACATTCCCAACCGCGTGGCACAACAACTGGCGGG
CAAACAGTCGTTGCTGATTGGCGTTGCCACCTCCAGTCTGGCCCTGCACG
```

```
CGCCGTCGCAAATTGTCGCGGCGATTAAATCTCGCGCCGATCAACTGGGT
GCCAGCGTGGTGGTGTCGATGGTAGAACGAAGCGGCGTCGAAGCCTGTAA
AGCGGCGGTGCACAATCTTCTCGCGCAACGCGTCAGTGGGCTGATCATTA
ACTATCCGCTGGATGACCAGGATGCCATTGCTGTGGAAGCTGCCTGCACT
AATGTTCCGGCGTTATTTCTTGATGTCTCTGACCAGACACCCATCAACAG
TATTATTTTCTCCCATGAAGACGGTACGCGACTGGGCGTGGAGCATCTGG
TCGCATTGGGTCACCAGCAAATCGCGCTGTTAGCGGGCCCATTAAGTTCT
GTCTCGGCGCGTCTGCGTCTGGCTGGCTGGCATAAATATCTCACTCGCAA
TCAAATTCAGCCGATAGCGGAACGGGAAGGCGACTGGAGTGCCATGTCCG
GTTTTCAACAAACCATGCAAATGCTGAATGAGGGCATCGTTCCCACTGCG
ATGCTGGTTGCCAACGATCAGATGGCGCTGGGCGCAATGCGCGCCATTAC
CGAGTCCGGGCTGCGCGTTGGTGCGGATATCTCGGTAGTGGGATACGACG
ATACCGAAGACAGCTCATGTTATATCCCGCCGTCAACCACCATCAAACAG
GATTTTCGCCTGCTGGGGCAAACCAGCGTGGACCGCTTGCTGCAACTCTC
TCAGGGCCAGGCGGTGAAGGGCAATCAGCTGTTGCCCGTCTCACTGGTGA
AAAGAAAAACCACCCTGGCGCCCAATACGCAAACCGCCTCTCCCCGCGCG
TTGGCCGATTCATTAATGCAGCTGGCACGACAGGTTTCCCGACTGGAAAG
CGGGCAGTGAGCGCAACGCAATTAATGTGAGTTAGCTCACTCATTAGGCA
CCCCAGGCTTTACACTTTATGCTTCCGGCTCGTATGTTGTGTGGAATTGT
GAGCGGATAACAATTTCACACAGGAAACAGCTATGACCATGATTACGGAT
TCACTGGCCGTCGTTTTACAACGTCGTGACTGGGAAAACCCTGGCGTTAC
CCAACTTAATCGCCTTGCAGCACATCCCCCTTTCGCCAGCTGGCGTAATA
GCGAAGAGGCCCGCACCGATCGCCCTTCCCAACAGTTGCGCAGCCTGAAT
GGCGAATGGCGCTTTGCCTGGTTTCCGGCACCAGAAGCGGTGCCGGAAAG
CTGGCTGGAGTGCGATCTTCCTGAGGCCGATACTGTCGTCGTCCCCTCAA
ACTGGCAGATGCACGGTTACGATGCGCCCATCTACACCAACGTAACCTAT
CCCATTACGGTCAATCCGCCGTTTGTTCCCACGGAGAATCCGACGGGTTG
TTACTCGCTCACATTTAATGTTGATGAAAGCTGGCTACAGGAAGGCCAGA
CGCGAATTATTTTTGATGGCGTTGGAATT
```

Anti-NKG2D heavy chain DNA sequence
(SEQ ID NO: 3)

```
CAAGTGCAGC TGGTTGAATC CGGTGGCGGT CTGGTCAAGC
CGGGCGGCTC TTTGCGTCTG AGCTGTGCCG CGTCGGGTTT
TACCTTCAGC TCTTATGGTA TGCATTGGGT GCGTCAGGCG
CCTGGCAAAG GTCTGGAGTG GGTTGCGTTC ATCCGCTACG
ATGGGTCTAA CAAATATTAT GCCGACTCAG TAAAAGGACG
CTTCACTATT AGCCGCGACA ATAGCAAAAA TACCCTGTAC
CTGCAAATGA ATAGCCTGCG CGCCGAAGAT ACCGCCGTTT
ACTATTGCGC TAAAGATCGT GGCCTGGGTG ATGGTACGTA
CTTCGATTAC TGGGGTCAGG GCACCACCGT TACCGTTAGT TCA
```

Anti-NKG2D light chain DNA sequence
(SEQ ID NO: 4)
CAGTCAGCGC TTACGCAGCC GGCGTCGGTG TCGGGTTCCC

CGGGTCAGTC GATCACGATC AGCTGTAGTG GGAGCAGCTC

CAACATCGGT AACAACGCAG TGAACTGGTA TCAGCAACTG

CCGGGAAAAG CGCCGAAACT GCTGATTTAC TATGATGATT

TGCTGCCAAG TGGAGTTAGT GACCGCTTTT CCGGCAGTAA

ATCGGGTACC TCGGCTTTTC TGGCTATTTC GGGTCTCCAG

AGCGAGGATG AAGCTGATTA TTATTGCGCC GCATGGGATG

ATAGCTTAAA TGGCCCAGTT TTTGGCGGCG GTACTAAACT

GACCGTGCTG

Anti-NKG2D heavy chain protein sequence
(SEQ ID NO: 5)
QVQLVESGGGLVKPGGSLRLSCAASGFTFS SYGMH

WVRQAPGKGLEWVA FIRYDGSNKYYADSVKG

RFTISRDNSKNTLYLQMNSLRAEDTAVYYCAK DRGLGDGTYFDY

WGQGTTVTVSS

Anti-NKG2D Light chain protein sequence
(SEQ ID NO: 6)
QSALTQPASVSGSPGQSITISC SGSSSNIGNNAVN

WYQQLPGKAPKLLIY YDDLLPS

GVSDRFSGSKSGTSAFLAISGLQSEDEADYYCAAWDDSLNGPV

FGGGTKLTVL

ScFv linker(G4S)3 DNA sequence
(SEQ ID NO: 7)
GGTGGGGGCG GCTCTGGTGG CGGTGGCAGC GGCGGAGGTG

GCAGT

ScFv linker(G4S)3 protein sequence
(SEQ ID NO: 8)
GGGGSGGGGS GGGGS

DNA sequence of HMA
(SEQ ID NO: 9)
CCGAGCGGCC AGGCGGGCGC GGCGGCATCG GAGTCCCTGT

TTGTGTCAAA TCACGCCTAC

Protein sequence of HMA
(SEQ ID NO: 10)
PSGQAGAAASESLFVSNHAY

3' to 5' CS-1 scFv heavy chain DATA sequence
(SEQ ID NO: 11)
AGCGTTACCG TGAGTACAGG CCAGGGCTGG TATGACATGG

CACGTACAGC CATCATGACC TCGCGCGCAT GTTACTACGT

CGCGTCAGAT GAATCGACGC CTTCCTCGCT GCAAATGTAT

GCAACCTCCA GCAGCAAAGA TGTTACCCTG ACCGCAAAGG

ACAAGTTTAA ACAGAATTTG CGTACGGAGA GTGACTCCCC

GCACATCATG GAATCTGGG AGTTGGGTCA GGGGCCTCGT

CAGAAGGTAT GGAACATGTG GTATACAACT TTTTCGTACG

GCTCAGCAAA ATGCAGCTTG AAAGTGTCGG CAGGTCCGCG

CGTGCTGGAG GCCGGTCCGC AGCAGCTGCA AGTCCAGTCT

3' to 5' CS-1 scFv light chain DNA sequence
(SEQ ID NO: 12)
AAACTTGAGT TGAAGACCGG TGCCGGCTTC ACCTTACCGA

CCAGTTATCA TCAACAATGC TATTACGTGG CCCTGGACGA

AGCACAGGTG AATTCAATTA CGTTTACGTT TGATACCGGC

TCTGGCAGCG GTACATTTCG TGATCCCGTG GGCACTTACC

GCTATTCGGC GAGTTATATC TTGCTGAAAC CTTCCCAAGG

TCCGAAACAG CAGTACTGGG CGGTTGGCAC CATTGTAGAC

CAATCAGCCA AATGTACAAT CTCGGTTCGC GATGGTGTCA

GTACGTCGAT GTCTAAGCAG TCACAGACAA TGGTTATCGA T

3' to 5' CS-1 scFv heavy chain protein sequence
(SEQ ID NO: 13)
SVTVSTGQGWYDMARTAIMTSRACYYVASDESTPSSLQMYATSSSKDVTL

TAKDKFKQNLRTESDSPHIMGIWELGQGPRQKVWNMWYTTFSYGSAKCSL

KVSAGPRVLEAGPQQLQVQS

3' to 5' CS-1 scFv light chain protein sequence
(SEQ ID NO: 14)
KLELKTGAGFTLPTSYHQQCYYVALDEAQVNSITFTFDTGSGSGTFRDPV

GTYRYSASYILLKPSQGPKQQYWAVGTIVDQSAKCTISVRDGVSTSMSKQ

SQTMVID

Histidine tag DNA sequence
(SEQ ID NO: 15)
CATCACCATC ATCACCAC

Histidine tag protein sequence
(SEQ ID NO: 16)
HHHHHH

3' to 5' EGFRvIII scFv heavy chain DNA sequence
(SEQ ID NO: 17)
AGTAGCGTGA CTGTTCTGAC GGGACAGGGT TGGTATGAGT

CTTGGGGTTC CTCCGGCGCG TGTTACTATG TTGCGACCGA

TGAAGCGCGC TTGAGCAATA TGCAACTGTA CCTTACTAAC

AAGAGTAATG ACCGTTCCAT CACGTTTCGG GGCAAAGTTA

GCGACGCATA TAATACCTCA GGTGGCAGCG GGTCTATCGC

AAGCGTCTGG GAGCTCGGTA AAGGCCCCGC ACAACGTGTG

TGGAGTATGG CTTACAGTAG CTTTACTTTC GGATCTGCTG

CATGCTCCCT GCGCCTGTCC GGAGGGCCAC AGGTTCTGGG

TGGTGGCAGT GAACTGGTCC AGGTGGAG

3' to 5' EGERvIII scFv light chain DNA sequence
(SEQ ID NO: 18)
TCAAATCACG CCTACAAAAT TGAAGTGAAA ACGGGGGCG

GTAGTACGTT GCCGTATTCC CACCATCAGC TGTGTTATTA

TACAGCATTC GACGAGCCTC AATTATCATC TGTTATCCTG

ACCTTCGAAA CCGGATCTGG CTCTGGGACG TTCCGGTCTC

CGGTGGGCTC CCAGCTGAAC TCAGCCGCGT ATATTCTGCG

CAAACCAGCG AAAGGGCCGA ACAACAGTA CTGGGCCCTG

AACAATCGCA TTGGACAGTC GGCCCGTTGC ACGATCACCG

TCCGGGACGG AGTCAGTGCG AGCCTGAGTT CCCCGTCGCA

GACCATGCAG ATTGAT

3' to 5' EGFRvIII scFv heavy chain protein sequence (SEQ ID NO: 19)
SSVTVLTGQGWYESWGSSGACYYVATDEARLSNMQLYLTNKSNDRSITFR

GKVSDAYNTSGGSGSIASVWELGKGPAQRVWSMAYSSFTFGSAACSLRLS

GGPQVLGGGSELVQVE

3' to 5' EGFRvIII scFv light chain protein sequence (SEQ ID NO: 20)
SNHAYKIEVKTGGGSTLPYSHHQLCYYTAFDEPQLSSVILTFETGSGSGT

FRSPVGSQLNSAAYILRKPAKGPKQQYWALNNRIGQSARCTITVRDGVSA

SLSSPSQTMQID

TriCLE (SEQ ID NO: 21)
GTGGTGATGATGGTGATGGCTCTGTACCTGCAGCTGCTGCGGACCCGCCT

CAAGAACGCGCGGGCCGGCTGATACCTTCAGGGAACATTTGGCCGAACCA

TAGCTGAAGGTGGTGTACCACATGTTCCACACTTTCTGGCGGGGCCCTG

GCCCAGTTCCCAGATGCCCATGATATGTGGGCTATCGCTTTCGGTGCGCA

GATTCTGTTTAAATTTGTCTTTCGCAGTCAGAGTCACGTCTTTTGAAGAG

GAGGTGGCATACATTTGCAGAGAGGAAGGGGTCGACTCATCGCTGGCCAC

GTAATAGCACGCCCGCGATGTCATAATCGCGGTCCGTGCCATATCGTACC

ATCCTTGGCCCGTCGACACCGTCACGGAGCCCCTCCCCCGCTGCCCCA

CCGCCACTACCACCGCCGCCAGAGTCAATCACCATGGTTTGGGACTGCTT

GCTCATGGAGGTGCTAACTCCGTCGCGAACTGAAATTGTACATTTGGCAG

ACTGGTCCACGATCGTTCCCACCGCCCAGTACTGCTGTTTCGGACCCTGA

GAAGGTTTCAGAAGGATATAGCTTGCACTATACCGGTACGTACCTACCGG

ATCACGGAACGTACCGCTGCCTGATCCTGTATCAAAGGTAAAGGTAATAG

AGTTCACCTGCGCTTCGTCAAGCGCCACGTAATAGCACTGCTGGTGATAG

CTCGTAGGGAGGGTAAATCCCGCACCCGTCTTGAGTTCCAGTTTGTAGGC

GTGATTTGACACAAACAGGGACTCCGATGCCGCCGCGCCCGCCTGGCCGC

TCGGCAGCACGGTCAGTTTAGTACCGCCGCCAAAAACTGGGCCATTTAAG

CTATCATCCCATGCGGCGCAATAATAATCAGCTTCATCCTCGCTCTGGAG

ACCCGAAATAGCCAGAAAAGCCGAGGTACCCGATTTACTGCCGGAAAAGC

GGTCACTAACTCCACTTGGCAGCAAATCATCATAGTAAATCAGCAGTTTC

GGCGCTTTTCCCGGCAGTTGCTGATACCAGTTCACTGCGTTGTTACCGAT

GTTGGAGCTGCTCCCACTACAGCTGATCGTGATCGACTGACCCGGGGAAC

CCGACACCGACGCCGGCTGCGTAAGCGCTGACTGACTGCCACCTCCGCCG

CTGCCACCGCCACCAGAGCCGCCCCCACCTGAACTAACGGTAACGGTGGT

GCCCTGACCCCAGTAATCGAAGTACGTACCATCACCCAGGCCACGATCTT

TAGCGCAATAGTAAACGGCGGTATCTTCGGCGCGCAGGCTATTCATTTGC

AGGTACAGGGTATTTTTGCTATTGTCGCGGCTAATAGTGAAGCGTCCTTT

TACTGAGTCGGCATAATATTTGTTAGACCCATCGTAGCGGATGAACGCAA

CCCACTCCAGACCTTTGCCAGGCGCCTGACGCACCCAATGCATACCATAA

GAGCTGAAGGTAAAACCCGACGCGGCACAGCTCAGACGCAAAGAGCCGCC

CGGCTTGACCAGACCGCCACCGGATTCAACCAGCTG CACTTGCAT

Glycine-serine linker (SEQ ID NO: 22)
GGGGS

The TriCLE was designed in silico by joining heavy and light chain of an anti-NKG2D antibody by a scFv (G4S)4 linker, a 20 amino acid linker human muscle aldose, and heavy and light chains of an anti-CS1 antibody (Chu et al., Leukemia 28 (2014), 917-27 and Chu et al. Clin Cancer Res 20 (2014), 3989-4000). The design is showed in FIG. 1. The DNA and protein sequences of the anti-NKG2D scFv are listed above (SEQ NOs:3-6). To join the heavy and light chains in anti-NKG2D scFv and anti-CS1 scFv, a linker composed of repeats of glycine and serine were used (SEQ II) NOs:7 and 8). The DNA and protein sequences of HMA are listed as SEQ ID NOS. 9 and 10. The DNA (SEQ ID NOs:11 and 12) and protein (SEQ ID NOs: 13 and 14) sequences of anti-CS-1 scFvs were shown from 3' to 5'. The entire sequence is followed by six copies of histidine (SEQ ID NOs:15-16).

Figure 2:
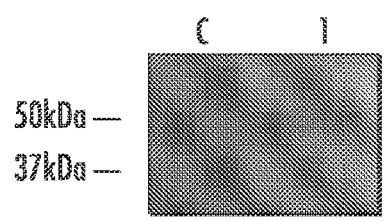
FIG. 2 shows a Western blot that confirms the purified protein is scFv containing anti-CS-1 TriCLE.

The biochemical analysis of the anti-CS-1 TriCLE showed it has a molecular weight of 56.6 kDa and had a pI of 7.99. The full amino acid composition is listed in Table 1. The size of the TriCLE was confirmed by standard. SDS-PAGE with Commassie Blue staining and western blot as detected by protein L (FIG. 2). The extinction coefficients for the TriCLE are 102720M-1cm-1 in water. The estimated half-life in bacteria is more than 10 hours.

TABLE 1

| Amino acid composition of TriCLE | | |
|---|---|---|
| Ala (A) | 345 | 21.6% |
| Arg (R) | 0 | 0.0% |
| Asn (N) | 0 | 0.0% |
| Asp (D) | 0 | 0.0% |
| Cys (C) | 409 | 25.6% |
| Gln (Q) | 0 | 0.0% |
| Glu (E) | 0 | 0.0% |
| Gly (G) | 484 | 30.3% |
| His (H) | 0 | 0.0% |
| Ile (I) | 0 | 0.0% |
| Leu (L) | 0 | 0.0% |
| Lys (K) | 0 | 0.0% |
| Met (M) | 0 | 0.0% |
| Phe (F) | 0 | 0.0% |
| Pro (P) | 0 | 0.0% |
| Ser (S) | 0 | 0.0% |
| Thr (T) | 361 | 22.6% |
| Trp (W) | 0 | 0.0% |
| Tyr (Y) | 0 | 0.0% |
| Val (V) | 0 | 0.0% |
| Pyl (O) | 0 | 0.0% |
| Sec (U) | 0 | 0.0% |
| (B) | 0 | 0.0% |
| (Z) | 0 | 0.0% |
| (X) | 0 | 0.0% |

Example 2: Cytotoxicity of Anti-CS-1 Tri-CLE Activated NK Cells Against Multiple Myeloma (MM) Cells FIG. 3 is a graph of the cytotoxicity of NK cell line NKL against multiple myeloma (MM) cell line H929 in the presence of anti-CS-1 Tri-CLE. Increasing doses of Tri-CLE ranged from 50 pg/mL to 10 ug/mL was added to the coculture of NKL: H929 at effector ratio of 20:1.

Example 3: Anti-CS-1 TriCLE can Stain Multiple Myeloma Cells Efficiently

When anti-CS-1 TriCLE was used as a staining reagent for flow cytometry, it could stain 80% of the MM1.s, a typical cell line isolated from a multiple myeloma patient (FIG. 4A). When compared with the isotype control, the mean fluorescence intensity was significantly increased. This suggests that the CS1 scFv was functional (FIG. 4B).

Example 4: Anti-CS-1 TriCLE Activated Human Killer Cells and Triggered Specific Cytotoxicity TriCLE at 5 µg/mL activated the primary T, NKT and NK cells in the PBMCs in 4 hours as indicated by the upregulation of CD69 (FIG. 5A). This suggested the anti-NKG2D scFv was immobilized and functional to trigger cell activation. The upregulation of the CD69 was observed when anti-CD3 antibody was administered at the same time (FIG. 5B). When TriCLE was used in co-culture of multiple myeloma cell lines such as MM1.s, H929 and RPMI-8226, the cytotoxicity from the TriCLE-activated PBMCs was increased (FIG. 5C). The $EC_{50}$ for MM1.s was $3\times10^{-12}$M. For those cell lines with low CS1 expression, the $EC_{50}$ for H929 cells was $1.2\times10^{-9}$ M and that for RPMI-8226 was $1.8\times10^{-9}$ M. TriCLE induced cytotoxicity using CD56 depleted effector cells at 24 h and 48 h (FIG. 5D).

Figure 6A:
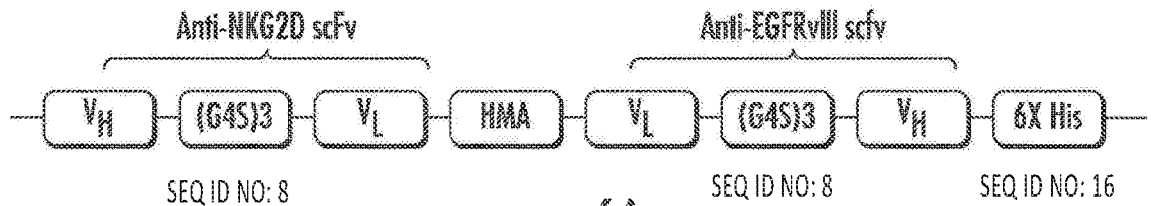
FIG. 6A shows a graphical display of anti-EGFRvIII TriCLE. $V_H$: heavy chain; $V_L$: Light chain; (G4S)3 (SEQ ID NO: 8): Glycine-Serine Linker; HMA: human muscle aldose; 6XHis (SEQ ID NO: 16): 6 repeats of histidine. The entire sequence was cloned into the pGEX6p 1m vector.
Figure 6B:
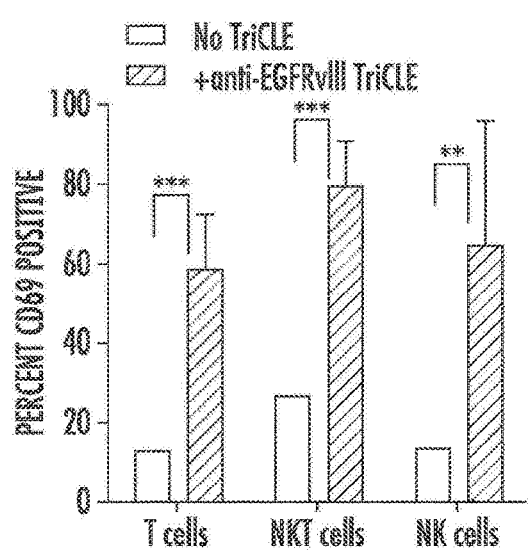
FIG. 6B shows the activation of T, NKT and NK cells by anti-EGFRvIII TriCLE. 5 ug/mL TriCLE was added to the resting human PBMCs for 4 hours and then the cells were harvested and stained for CD3, CD56, CD14 and CD69 for 20 min at room temperature. The cells were analyzed by flow cytometry.
Figure 6C:
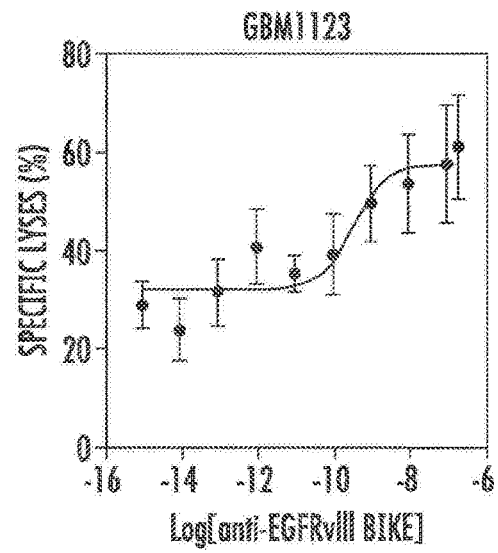
FIG. 6C shows the cytotoxicity of activated human PBMCs was enhanced by TriCLE against three multiple myeloma cells GBM1123. The EC50 was calculated from the non-linear regression curves. Results were from three independent donors. *p<0.001; p<0.01.

Example 5: Anti-EGFRvIII TriCLE Activated Human Killer Cells and Triggered Specific Cytotoxicity FIG. 1A shows a graphical display of anti-EGFRvIII Tri-CLE. The DNA and protein sequences for the heavy and light chains of the EGFRvIII scFv are shown as SEQ ID NOs:17-20. FIG. 6A shows the activation of T, NKT and NK cells by anti-EGFRvIII TriCLE. 5 µg/mL TriCLE was added to the resting human PBMCs for 4 hours and then the cells were harvested and stained for CD3, CD56, CD14 and CD69 for 20 min at room temperature. The cells were analyzed by flow cytometry. FIG. 6B shows that the cytotoxicity of activated human PBMCs was enhanced by anti-EGFRvIII TriCLE against three multiple myeloma cells GBM1123. The EC50 was calculated from the non-linear regression curves. Results were from three independent donors. *$p<0.001$; $p<0.01$.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A polypeptide comprising a first antigen-binding region comprising a variable heavy ($V_H$) domain comprising the amino acid sequence of SEQ ID NO: 5 and a variable light ($V_L$) domain comprising amino acid sequence of SEQ ID NO: 6 that binds NKG2D receptor and a second antigen-binding region comprising a variable heavy ($V_H$) domain comprising the amino acid sequence of SEQ ID NO:13 and a variable light ($V_L$) domain comprising the amino acid sequence of SEQ ID NO:14 that binds CS 1.

2. The polypeptide of claim 1, wherein the second antigen-binding region binds CS-1 and comprises a single chain variable fragment.

3. The polypeptide of claim 1, further comprising a non-immunogenic linker.

4. The polypeptide of claim 1, comprising the following formula:

$V_L N$-$V_H N$-$V_L T$-$V_H T$, $V_H N$-$V_L N$-$V_H T$-$V_L T$, $V_L N$-$V_H N$-$V_H T$-$V_L T$, or $V_H N$-$V_L N$-$V_L T$-$V_H T$, wherein "$V_H T$" is the heavy chain variable domain specific for CS1;
wherein "$V_L T$" is the light chain variable domain specific for CS-1;
wherein "$V_L N$" is the light chain variable domain specific for NKG2D receptor;
wherein "$V_H N$" is the heavy chain variable domain specific for NKG2D receptor;
wherein "-" consists of a peptide linker or a peptide bond;
wherein "-" consists of a peptide linker or a peptide bond; and
wherein each formula is from the N-terminus to the C-terminus.

5. A bispecific antibody comprising a single polypeptide chain comprising a first antigen-binding region and a second antigen-binding region;
wherein the first antigen-binding region comprises the amino acid sequence of SEQ ID NO:5 and the amino acid sequence of SEQ ID NO:6 and is capable of recruiting the activity of a human immune effector cell by specifically binding to NKG2D receptor on the human immune effector cell; and
wherein the second antigen-binding region comprises a variable heavy ($V_H$) domain comprising the amino acid sequence of SEQ ID NO:13 and a variable light ($V_L$) domain comprising the amino acid sequence of SEQ ID NO:14 and is capable of specifically binding to CS- 1 on a target cell.

6. A pharmaceutical composition comprising the bispecific antibody of claim 5 in a pharmaceutically acceptable carrier.

7. A method for treating a CS-1 expressing cancer in a subject, comprising administering to the subject a therapeutically effective amount of the pharmaceutical composition of claim 6.

8. An isolated polynucleotide, comprising a nucleic acid sequence encoding the polypeptide of claim 1 or claim 4.

9. An isolated expression vector comprising the polynucleotide of claim 8 operably linked to a heterologous expression control sequence.

10. An isolated host cell comprising the vector of claim 9.

11. The polypeptide of claim 3, wherein the non-immunogenic linker comprises a fragment of human muscle aldose protein.

12. The polypeptide of claim 11, wherein the non-immunogenic linker comprises SEQ ID NO: 10.

13. The polypeptide of claim 4, wherein "-" comprises a non-immunogenic linker.

14. The polypeptide of claim 13, wherein the non-immunogenic linker comprises SEQ ID NO: 10.

* * * * *

SEQUENCE LISTING

```
<160> NUMBER OF SEQ ID NOS: 22

<210> SEQ ID NO 1
<211> LENGTH: 6898
<212> TYPE: DNA
<213> ORGANISM: Artificial Sequence
<220> FEATURE:
<223> OTHER INFORMATION: Synthetic Construct

<400> SEQUENCE: 1
atccggatat agttcctcct ttcagcaaaa aaccccctcaa gacccgttta gaggccccaa      60
ggggttatgc tagttattgc tcagcggtgg cagcagccaa ctcagcttcc tttcgggctt     120
tgttagcagc cggatctcag cggccgcgtg gtgatgatgg tgatggctct gtacctgcag     180
ctgctgcgga cccgcctcaa gaacgcgcgg gccggctgat accttcaggg aacatttggc     240
cgaaccatag ctgaaggtgg tgtaccacat gttccacact ttctggcggg ggccctggcc     300
cagttcccag atgcccatga tatgtgggct atcgctttcg gtgcgcagat tctgtttaaa     360
tttgtctttc gcagtcagag tcacgtcttt tgaagaggag gtggcataca tttgcagaga     420
ggaaggggtc gactcatcgc tggccacgta atagcacgcc cgcgatgtca taatcgcggt     480
ccgtgccata tcgtaccatc cttggcccgt cgacaccgtc acggagcccc ctcccccgct     540
gcccccaccg ccactaccac cgccgccaga gtcaatcacc atggtttggg actgcttgct     600
catggaggtg ctaactccgt cgcgaactga aattgtacat ttggcagact ggtccacgat     660
cgttcccacc gcccagtact gctgtttcgg accctgagaa ggtttcagaa ggatatagct     720
tgcactatac cggtacgtac ctaccggatc acggaacgta ccgctgcctg atcctgtatc     780
aaaggtaaag gtaatagagt tcacctgcgc ttcgtcaagc gccacgtaat agcactgctg     840
gtgatagctc gtagggaggg taaatcccgc acccgtcttg agttccagtt tgtaggcgtg     900
```

```
atttgacaca aacagggact ccgatgccgc cgcgcccgcc tggccgctcg gcagcacggt      960
cagtttagta ccgccgccaa aaactgggcc atttaagcta tcatcccatg cggcgcaata     1020
ataatcagct tcatcctcgc tctggagacc cgaaatagcc agaaaagccg aggtacccga     1080
tttactgccg gaaaagcggt cactaactcc acttggcagc aaatcatcat agtaaatcag     1140
cagtttcggc gcttttcccg gcagttgctg ataccagttc actgcgttgt taccgatgtt     1200
ggagctgctc ccactacagc tgatcgtgat cgactgaccc ggggaacccg acaccgacgc     1260
cggctgcgta agcgctgact gactgccacc tccgccgctg ccaccgccac cagagccgcc     1320
cccacctgaa ctaacggtaa cggtggtgcc ctgaccccag taatcgaagt acgtaccatc     1380
acccaggcca cgatctttag cgcaatagta aacggcggta tcttcggcgc gcaggctatt     1440
catttgcagg tacagggtat ttttgctatt gtcgcggcta atagtgaagc gtccttttac     1500
tgagtcggca taatatttgt tagacccatc gtagcggatg aacgcaaccc actccagacc     1560
tttgccaggc gcctgacgca cccaatgcat accataagag ctgaaggtaa acccgacgc     1620 ggcacagctc agacgcaaag agccgcccgg cttgaccaga ccgccaccgg attcaaccag     1680
ctgcacttgc atgaattcta tatctccttc ttaaagttaa acaaaattat ttctagaggg     1740
gaattgttat ccgctcacaa ttcccctata gtgagtcgta ttaatttcgc gggatcgaga     1800
tctcgatcct ctacgccgga cgcatcgtgg ccggcatcac cggcgccaca ggtgcggttg     1860
ctggcgccta tatcgccgac atcaccgatg gggaagatcg ggctcgccac ttcgggctca     1920
tgagcgcttg tttcggcgtg ggtatggtgg caggccccgt ggccggggga ctgttgggcg     1980
ccatctcctt gcatgcacca ttccttgcgg cggcggtgct caacggcctc aacctactac     2040
tgggctgctt cctaatgcag gagtcgcata agggagagcg tcgagatccc ggacaccatc     2100
gaatggcgca aaacctttcg cggtatggca tgatagcgcc cggaagagag tcaattcagg     2160
gtggtgaatg tgaaaccagt aacgttatac gatgtcgcag agtatgccgg tgtctcttat     2220
cagaccgttt cccgcgtggt gaaccaggcc agccacgttt ctgcgaaaac gcgggaaaaa     2280
gtggaagcgg cgatgcggag ctgaattac attcccaacc gcgtggcaca acaactggcg     2340
ggcaaacagt cgttgctgat tggcgttgcc acctccagtc tggccctgca cgcgccgtcg     2400
caaattgtcg cggcgattaa atctcgcgcc gatcaactgg gtgccagcgt ggtggtgtcg     2460
atggtagaac gaagcggcgt cgaagcctgt aaagcggcgg tgcacaatct tctcgcgcaa     2520
cgcgtcagtg ggctgatcat taactatccg ctggatgacc aggatgccat tgctgtggaa     2580
gctgcctgca ctaatgttcc ggcgttattt cttgatgtct ctgaccagac acccatcaac     2640
agtattattt ctcccatga agacggtacg cgactgggcg tggagcatct ggtcgcattg     2700
ggtcaccagc aaatcgcgct gttagcgggc ccattaagtt ctgtctcggc gcgtctgcgt     2760
ctggctggct ggcataaata tctcactcgc aatcaaattc agccgatagc ggaacgggaa     2820
ggcgactgga gtgccatgtc cggttttcaa caaaccatgc aaatgctgaa tgagggcatc     2880
gttcccactg cgatgctggt tgccaacgat cagatggcgc tgggcgcaat gcgcgccatt     2940
accgagtccg gctgcgcgt tggtgcggat atctcggtag tgggatacga cgataccgaa     3000
gacagctcat gttatatccc gccgttaacc accatcaaac aggattttcg cctgctgggg     3060
caaaccagcg tggaccgctt gctgcaactc tctcagggcc aggcggtgaa gggcaatcag     3120
ctgttgcccg tctcactggt gaaaagaaaa accaccctgg cgcccaatac gcaaaccgcc     3180
tctccccgcg cgttggccga ttcattaatg cagctggcac gacaggtttc ccgactggaa     3240
```

-continued

```
agcgggcagt gagcgcaacg caattaatgt aagttagctc actcattagg caccgggatc    3300
tcgaccgatg cccttgagag ccttcaaccc agtcagctcc ttccggtggg cgcggggcat    3360
gactatcgtc gccgcactta tgactgtctt ctttatcatg caactcgtag acaggtgcc     3420 ggcagcgctc tgggtcattt tcggcgagga ccgctttcgc tggagcgcga cgatgatcgg    3480
cctgtcgctt gcggtattcg gaatcttgca cgccctcgct caagccttcg tcactggtcc    3540
cgccaccaaa cgtttcggcg agaagcaggc cattatcgcc ggcatggcgg ccccacgggt    3600
gcgcatgatc gtgctcctgt cgttgaggac ccggctaggc tggcggggtt gccttactgg    3660
ttagcagaat gaatcaccga tacgcgagcg aacgtgaagc gactgctgct gcaaaacgtc    3720
tgcgacctga gcaacaacat gaatggtctt cggtttccgt gtttcgtaaa gtctggaaac    3780
gcggaagtca gcgccctgca ccattatgtt ccggatctgc atcgcaggat gctgctggct    3840
accctgtgga acacctacat ctgtattaac gaagcgctgg cattgaccct gagtgatttt    3900
tctctggtcc cgccgcatcc ataccgccag ttgtttaccc tcacaacgtt ccagtaaccg    3960
ggcatgttca tcatcagtaa cccgtatcgt gagcatcctc tctcgtttca tcggtatcat    4020
tacccccatg aacagaaatc ccccttacac ggaggcatca gtgaccaaac aggaaaaaac    4080
cgcccttaac atgcccgct ttatcagaag ccagacatta acgcttctgg agaaactcaa     4140
cgagctggac gcggatgaac aggcagacat ctgtgaatcg cttcacgacc acgctgatga    4200
gctttaccgc agctgcctcg cgcgtttcgg tgatgacggt gaaaacctct gacacatgca    4260
gctcccggag acggtcacag cttgtctgta agcggatgcc gggagcagac aagcccgtca    4320
gggcgcgtca gcgggtgttg gcgggtgtcg ggcgcagcc atgacccagt cacgtagcga     4380
tagcggagtg tatactggct taactatgcg gcatcagagc agattgtact gagagtgcac    4440
catatatgcg gtgtgaaata ccgcacagat gcgtaaggag aaaataccgc atcaggcgct    4500
cttccgcttc ctcgctcact gactcgctgc gctcggtcgt tcggctgcgg cgagcggtat    4560
cagctcactc aaaggcggta atacggttat ccacagaatc aggggataac gcaggaaaga    4620
acatgtgagc aaaaggccag caaaaggcca ggaaccgtaa aaaggccgcg ttgctggcgt    4680
ttttccatag gctccgcccc cctgacgagc atcacaaaaa tcgacgctca agtcagaggt    4740
ggcgaaaccc gacaggacta taaagatacc aggcgtttcc ccctggaagc tccctcgtgc    4800
gctctcctgt tccgaccctg ccgcttaccg gatacctgtc gcctttctc ccttcgggaa     4860 gcgtggcgct ttctcatagc tcacgctgta ggtatctcag ttcggtgtag tcgttcgct    4920 ccaagctggg ctgtgtgcac gaaccccccg ttcagcccga ccgctgcgcc ttatccggta    4980
actatcgtct tgagtccaac ccggtaagac acgacttatc gccactggca gcagccactg    5040
gtaacaggat tagcagagcg aggtatgtag gcggtgctac agagttcttg aagtggtggc    5100
ctaactacgg ctacactaga aggacagtat ttggtatctg cgctctgctg aagccagtta    5160
ccttcggaaa aagagttggt agctcttgat ccggcaaaca accaccgct ggtagcggtg     5220 gtttttttgt ttgcaagcag cagattacgc gcagaaaaaa aggatctcaa gaagatcctt    5280
tgatcttttc tacggggtct gacgctcagt ggaacgaaaa ctcacgttaa gggattttgg    5340
tcatgagatt atcaaaaagg atcttcacct agatcctttt aaattaaaaa tgaagtttta    5400
aatcaatcta aagtatatat gagtaaactt ggtctgacag ttaccaatgc ttaatcagtg    5460
aggcacctat ctcagcgatc tgtctatttc gttcatccat agttgcctga ctccccgtcg    5520
tgtagataac tacgatacgg gagggcttac catctggccc cagtgctgca atgataccgc    5580
gagacccacg ctcaccggct ccagatttat cagcaataaa ccagccagcc ggaagggccg    5640
```

-continued

| | |
|---|---|
| agcgcagaag tggtcctgca actttatccg cctccatcca gtctattaat tgttgccggg | 5700 |
| aagctagagt aagtagttcg ccagttaata gtttgcgcaa cgttgttgcc attgctgcag | 5760 |
| gcatcgtggt gtcacgctcg tcgtttggta tggcttcatt cagctccggt tcccaacgat | 5820 |
| caaggcgagt tacatgatcc cccatgttgt gcaaaaaagc ggttagctcc ttcggtcctc | 5880 |
| cgatcgttgt cagaagtaag ttggccgcag tgttatcact catggttatg gcagcactgc | 5940 |
| ataattctct tactgtcatg ccatccgtaa gatgcttttc tgtgactggt gagtactcaa | 6000 |
| ccaagtcatt ctgagaatag tgtatgcggc gaccgagttg ctcttgcccg gcgtcaatac | 6060 |
| gggataatac cgcgccacat agcagaactt taaaagtgct catcattgga aaacgttctt | 6120 |
| cggggcgaaa actctcaagg atcttaccgc tgttgagatc cagttcgatg taacccactc | 6180 |
| gtgcacccaa ctgatcttca gcatctttta ctttcaccag cgtttctggg tgagcaaaaa | 6240 |
| caggaaggca aaatgccgca aaaaagggaa taagggcgac acggaaatgt tgaatactca | 6300 |
| tactcttcct ttttcaatat tattgaagca tttatcaggg ttattgtctc atgagcggat | 6360 |
| acatatttga atgtatttag aaaaataaac aaataggggt tccgcgcaca tttccccgaa | 6420 |
| aagtgccacc tgaaattgta acgttaata ttttgttaaa attcgcgtta aattttgtt | 6480 |
| aaatcagctc attttttaac caataggccg aaatcggcaa aatcccttat aaatcaaaag | 6540 |
| aatagaccga gatagggttg agtgttgttc cagtttggaa caagagtcca ctattaaaga | 6600 |
| acgtggactc caacgtcaaa gggcgaaaaa ccgtctatca gggcgatggc ccactacgtg | 6660 |
| aaccatcacc ctaatcaagt tttttggggt cgaggtgccg taaagcacta aatcggaacc | 6720 |
| ctaaagggag cccccgattt agagcttgac ggggaaagcc ggcgaacgtg gcgagaaagg | 6780 |
| aagggaagaa agcgaaagga gcgggcgcta gggcgctggc aagtgtagcg gtcacgctgc | 6840 |
| gcgtaaccac cacacccgcc gcgcttaatg cgccgctaca ggcgcgtccc attcgcca | 6898 |

<210> SEQ ID NO 2
<211> LENGTH: 5828
<212> TYPE: DNA
<213> ORGANISM: Artificial Sequence
<220> FEATURE:
<223> OTHER INFORMATION: Synthetic Construct

<400> SEQUENCE: 2

| | |
|---|---|
| acgttatcga ctgcacggtg caccaatgct tctggcgtca ggcagccatc ggaagctgtg | 60 |
| gtatggctgt gcaggtcgta aatcactgca taattcgtgt cgctcaaggc gcactcccgt | 120 |
| tctggataat gttttttgcg ccgacatcat aacggttctg gcaaatattc tgaaatgagc | 180 |
| tgttgacaat taatcatcgg ctcgtataat gtgtggaatt gtgagcggat aacaatttca | 240 |
| cacaggaaac agtattcgga tccccggaat tcatgcaagt gcagctggtt gaatccggtg | 300 |
| gcggtctggt caagccgggc ggctcttttg cgtctgagct gccgcgtcg gttttacct | 360 |
| tcagctctta tggtatgcat tgggtgcgtc aggcgcctgg caaaggtctg gagtgggttg | 420 |
| cgttcatccg ctacgatggg tctaacaaat attatgccga ctcagtaaaa ggacgcttca | 480 |
| ctattagccg cgacaatagc aaaaatacccc tgtacctgca aatgaatagc ctgcgcgccg | 540 |
| aagataccgc cgtttactat tgcgctaaag atcgtgcct gggtgatggt acgtacttcg | 600 |
| attactgggg tcagggcacc accgttaccg ttagttcagg tggggcggc tctggtggcg | 660 |
| gtggcagcgg cggaggtggc agtcagtcag cgcttacgca gccggcgtcg gtgtcgggtt | 720 |
| ccccgggtca gtcgatcacg atcagctgta gtggagcag ctccaacatc ggtaacaacg | 780 |

```
cagtgaactg gtatcagcaa ctgccgggaa aagcgccgaa actgctgatt tactatgatg      840
atttgctgcc aagtggagtt agtgaccgct tttccggcag taaatcgggt acctcggctt      900
ttctggctat ttcgggtctc cagagcgagg atgaagctga ttattattgc gccgcatggg      960
atgatagctt aaatggccca gttttttggcg gcggtactaa actgaccgtg ctgccgagcg     1020
gccaggcggg cgcggcggca tcggagtccc tgtttgtgtc aaatcacgcc tacaaactgg     1080
aactcaagac gggtgcggga tttaccctcc ctacgagcta tcaccagcag tgctattacg     1140
tggcgcttga cgaagcgcag gtgaactcta ttacctttac ctttgataca ggatcaggca     1200
gcggtacgtt ccgtgatccg gtaggtacgt accggtatag tgcaagctat atccttctga     1260
aaccttctca gggtccgaaa cagcagtact gggcggtggg aacgatcgtg gaccagtctg     1320
ccaaatgtac aatttcagtt cgcgacgagt tagcacctc catgagcaag cagtcccaaa      1380
ccatggtgat tgactctggc ggcggtggta gtggcggtgg gggcagcggg ggagggggct     1440
ccgtgacggt gtcgacgggc caaggatggt acgatatggc acggaccgcg attatgacat     1500
cgcgggcgtg ctattacgtg gccagcgatg agtcgacccc ttcctctctg caaatgtatg     1560
ccacctcctc ttcaaaagac gtgactctga ctgcgaaaga caaatttaaa cagaatctgc     1620
gcaccgaaag cgatagccca catatcatgg gcatctggga actgggccag ggcccccgcc     1680
agaaagtgtg gaacatgtgg tacaccacct tcagctatgg ttcggccaaa tgttccctga     1740
aggtatcagc cggcccgcgc gttcttgagg cgggtccgca gcagctgcag gtacagagcc     1800
atcaccatca tcaccacgcg gccgcatcgt gactgactga cgatctgcct cgcgcgtttc     1860
ggtgatgacg gtgaaaacct ctgacacatg cagctcccgg agacggtcac agcttgtctg     1920
taagcggatg ccgggagcag acaagcccgt cagggcgcgt cagcgggtgt ggcgggtgt     1980 cggggcgcag ccatgaccca gtcacgtagc gatagcggag tgtataattc ttgaagacga     2040
aagggcctcg tgatacgcct attttttatag gttaatgtca tgataataat ggtttcttag     2100
acgtcaggtg gcacttttcg gggaaatgtg cgcggaaccc ctatttgttt attttttctaa     2160 atacattcaa atatgtatcc gctcatgaga caataaccct gataaatgct tcaataatat     2220
tgaaaaagga agagtatgag tattcaacat ttccgtgtcg cccttattcc cttttttgcg     2280 gcatttttgcc ttcctgtttt tgctcaccca gaaacgctgg tgaaagtaaa agatgctgaa     2340
gatcagttgg gtgcacgagt gggttacatc gaactggatc tcaacagcgg taagatcctt     2400
gagagttttc gccccgaaga acgttttcca atgatgagca cttttaaagt tctgctatgt     2460
ggcgcggtat tatcccgtgt tgacgccggg caagagcaac tcggtcgccg catacactat     2520
tctcagaatg acttggttga gtactcacca gtcacagaaa agcatcttac ggatggcatg     2580
acagtaagag aattatgcag tgctgccata accatgagtg ataacactgc ggccaactta     2640
cttctgacaa cgatcggagg accgaaggag ctaaccgctt ttttgcacaa catgggggat     2700
catgtaactc gccttgatcg ttgggaaccg gagctgaatg aagccatacc aaacgacgag     2760
cgtgacacca cgatgcctgc agcaatggca acaacgttgc gcaaactatt aactggcgaa     2820
ctacttactc tagcttcccg gcaacaatta atagactgga tggaggcgga taaagttgca     2880
ggaccacttc tgcgctcggc ccttccggct ggctggttta ttgctgataa atctggagcc     2940
ggtgagcgtg ggtctcgcgg tatcattgca gcactggggc cagatggtaa gccctcccgt     3000
atcgtagtta tctacacgac ggggagtcag gcaactatgg atgaacgaaa tagacagatc     3060
gctgagatag gtgcctcact gattaagcat tggtaactgt cagaccaagt ttactcatat     3120
atactttaga ttgatttaaa acttcatttt taatttaaaa ggatctaggt gaagatccct     3180
```

```
tttgataatc tcatgaccaa aatcccttaa cgtgagtttt cgttccactg agcgtcagac    3240
cccgtagaaa agatcaaagg atcttcttga gatccttttt ttctgcgcgt aatctgctgc    3300
ttgcaaacaa aaaaaccacc gctaccagcg gtggtttgtt tgccggatca agagctacca    3360 actcttttc cgaaggtaac tggcttcagc agagcgcaga taccaaatac tgtccttcta    3420
gtgtagccgt agttaggcca ccacttcaag aactctgtag caccgcctac atacctcgct    3480
ctgctaatcc tgttaccagt ggctgctgcc agtggcgata gtcgtgtct taccgggttg    3540 gactcaagac gatagttacc ggataaggcg cagcggtcgg gctgaacggg gggttcgtgc    3600
acacagccca gcttggagcg aacgacctac accgaactga gatacctaca gcgtgagcta    3660
tgagaaagcg ccacgcttcc cgaagggaga aaggcggaca ggtatccggt aagcggcagg    3720
gtcggaacag gagagcgcac gagggagctt ccagggggaa acgcctggta tctttatagt    3780
cctgtcgggt ttcgccacct ctgacttgag cgtcgatttt tgtgatgctc gtcagggggg    3840
cggagcctat ggaaaaacgc cagcaacgcg gccttttac ggttcctggc cttttgctgg    3900
ccttttgctc acatgttctt tcctgcgtta tcccctgatt ctgtggataa ccgtattacc    3960
gcctttgagt gagctgatac cgctcgccgc agccgaacga ccgagcgcag cgagtcagtg    4020
agcgaggaag cggaagagcg cctgatgcgg tattttctcc ttacgcatct gtgcggtatt    4080
tcacaccgca taaattccga caccatcgaa tggtgcaaaa cctttcgcgg tatggcatga    4140
tagcgcccgg aagagagtca attcagggtg gtgaatgtga aaccagtaac gttatacgat    4200
gtcgcagagt atgccggtgt ctcttatcag accgtttccc gcgtggtgaa ccaggccagc    4260
cacgtttctg cgaaaacgcg ggaaaaagtg gaagcggcga tggcggagct gaattacatt    4320
cccaaccgcg tggcacaaca actggcgggc aaacagtcgt tgctgattgg cgttgccacc    4380
tccagtctgg ccctgcacgc gccgtcgcaa attgtcgcgg cgattaaatc tcgcgccgat    4440
caactgggtg ccagcgtggt ggtgtcgatg gtagaacgaa gcggcgtcga agcctgtaaa    4500
gcggcggtgc acaatcttct cgcgcaacgc gtcagtgggc tgatcattaa ctatccgctg    4560
gatgaccagg atgccattgc tgtggaagct gcctgcacta atgttccggc gttatttctt    4620
gatgtctctg accagacacc catcaacagt attatttct cccatgaaga cggtacgcga    4680
ctgggcgtgg agcatctggt cgcattgggt caccagcaaa tcgcgctgtt agcgggccca    4740
ttaagttctg tctcggcgcg tctgcgtctg gctggctggc ataaatatct cactcgcaat    4800
caaattcagc cgatagcgga acgggaaggc gactggagtg ccatgtccgg ttttcaacaa    4860
accatgcaaa tgctgaatga gggcatcgtt cccactgcga tgctggttgc caacgatcag    4920
atggcgctgg gcgcaatgcg cgccattacc gagtccgggc tgcgcgttgg tgcggatatc    4980
tcggtagtgg gatacgacga taccgaagac agctcatgtt atatcccgcc gtcaaccacc    5040
atcaaacagg attttcgcct gctggggcaa accagcgtgg accgcttgct gcaactctct    5100
cagggccagg cggtgaaggg caatcagctg ttgcccgtct cactggtgaa agaaaaaacc    5160
accctggcgc ccaatacgca aaccgcctct ccccgcgcgt tggccgattc attaatgcag    5220
ctggcacgac aggtttcccg actggaaagc gggcagtgag cgcaacgcaa ttaatgtgag    5280
ttagctcact cattaggcac cccaggcttt acactttatg cttccggctc gtatgttgtg    5340
tggaattgtg agcggataac aatttcacac aggaaacagc tatgaccatg attacggatt    5400
cactggccgt cgttttacaa cgtcgtgact gggaaaaccc tggcgttacc caacttaatc    5460
gccttgcagc acatccccct ttcgccagct ggcgtaatag cgaagaggcc cgcaccgatc    5520
```

```
gcccttccca acagttgcgc agcctgaatg gcgaatggcg ctttgcctgg tttccggcac    5580
cagaagcggt gccggaaagc tggctggagt gcgatcttcc tgaggccgat actgtcgtcg    5640
tcccctcaaa ctggcagatg cacggttacg atgcgcccat ctacaccaac gtaacctatc    5700
ccattacggt caatccgccg tttgttccca cggagaatcc gacgggttgt tactcgctca    5760
catttaatgt tgatgaaagc tggctacagg aaggccagac gcgaattatt tttgatggcg    5820
ttggaatt                                                             5828

<210> SEQ ID NO 3
<211> LENGTH: 363
<212> TYPE: DNA
<213> ORGANISM: Artificial Sequence
<220> FEATURE:
<223> OTHER INFORMATION: Synthetic Construct

<400> SEQUENCE: 3
caagtgcagc tggttgaatc cggtggcggt ctggtcaagc cgggcggctc tttgcgtctg     60
agctgtgccg cgtcgggttt taccttcagc tcttatggta tgcattgggt gcgtcaggcg    120
cctggcaaag gtctggagtg ggttgcgttc atccgctacg atgggtctaa caaatattat    180
gccgactcag taaaggacg cttcactatt agccgcgaca tagcaaaaa tacccctgtac    240 ctgcaaatga atagcctgcg cgccgaagat accgccgttt actattgcgc taaagatcgt    300
ggcctgggtg atggtacgta cttcgattac tggggtcagg gcaccaccgt taccgttagt    360
tca                                                                  363

<210> SEQ ID NO 4
<211> LENGTH: 330
<212> TYPE: DNA
<213> ORGANISM: Artificial Sequence
<220> FEATURE:
<223> OTHER INFORMATION: Synthetic Construct

<400> SEQUENCE: 4
cagtcagcgc ttacgcagcc ggcgtcggtg tcgggttccc cgggtcagtc gatcacgatc     60
agctgtagtg ggagcagctc caacatcggt aacaacgcag tgaactggta tcagcaactg    120
ccgggaaaag cgccgaaact gctgatttac tatgatgatt tgctgccaag tggagttagt    180
gaccgctttt ccggcagtaa atcgggtacc tcggcttttc tggctatttc gggtctccag    240
agcgaggatg aagctgatta ttattgcgcc gcatgggatg atagcttaaa tggcccagtt    300
tttggcggcg gtactaaact gaccgtgctg                                    330

<210> SEQ ID NO 5
<211> LENGTH: 121
<212> TYPE: PRT
<213> ORGANISM: Artificial Sequence
<220> FEATURE:
<223> OTHER INFORMATION: Synthetic Construct

<400> SEQUENCE: 5

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Gly Leu Gly Asp Gly Thr Tyr Phe Asp Tyr Trp Gly
            100                 105                 110

Gln Gly Thr Thr Val Thr Val Ser Ser
        115                 120

<210> SEQ ID NO 6
<211> LENGTH: 110
<212> TYPE: PRT
<213> ORGANISM: Artificial Sequence
<220> FEATURE:
<223> OTHER INFORMATION: Synthetic Construct

<400> SEQUENCE: 6

Gln Ser Ala Leu Thr Gln Pro Ala Ser Val Ser Gly Ser Pro Gly Gln
 1               5                  10                  15

Ser Ile Thr Ile Ser Cys Ser Gly Ser Ser Asn Ile Gly Asn Asn
                 20                  25                  30

Ala Val Asn Trp Tyr Gln Gln Leu Pro Gly Lys Ala Pro Lys Leu Leu
             35                  40                  45

Ile Tyr Tyr Asp Asp Leu Leu Pro Ser Gly Val Ser Asp Arg Phe Ser
 50                  55                  60

Gly Ser Lys Ser Gly Thr Ser Ala Phe Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Pro Val Phe Gly Gly Gly Thr Lys Leu Thr Val Leu
            100                 105                 110

<210> SEQ ID NO 7
<211> LENGTH: 45
<212> TYPE: DNA
<213> ORGANISM: Artificial Sequence
<220> FEATURE:
<223> OTHER INFORMATION: Synthetic Construct

<400> SEQUENCE: 7
ggtgggggcg gctctggtgg cggtggcagc ggcggaggtg gcagt          45

<210> SEQ ID NO 8
<211> LENGTH: 15
<212> TYPE: PRT
<213> ORGANISM: Artificial Sequence
<220> FEATURE:
<223> OTHER INFORMATION: Synthetic Construct

<400> SEQUENCE: 8

Gly Gly Gly Gly Ser Gly Gly Gly Gly Ser Gly Gly Gly Gly Ser
 1               5                  10                  15

<210> SEQ ID NO 9
<211> LENGTH: 60
<212> TYPE: DNA
<213> ORGANISM: Artificial Sequence
<220> FEATURE:
<223> OTHER INFORMATION: Synthetic Construct

<400> SEQUENCE: 9
```

```
ccgagcggcc aggcgggcgc ggcggcatcg gagtccctgt ttgtgtcaaa tcacgcctac    60
```

<210> SEQ ID NO 10
<211> LENGTH: 20
<212> TYPE: PRT
<213> ORGANISM: Artificial Sequence
<220> FEATURE:
<223> OTHER INFORMATION: Synthetic Construct

<400> SEQUENCE: 10

Pro Ser Gly Gln Ala Gly Ala Ala Ala Ser Glu Ser Leu Phe Val Ser
1               5                   10                  15

Asn His Ala Tyr
            20

<210> SEQ ID NO 11
<211> LENGTH: 360
<212> TYPE: DNA
<213> ORGANISM: Artificial Sequence
<220> FEATURE:
<223> OTHER INFORMATION: Synthetic Construct

<400> SEQUENCE: 11

```
agcgttaccg tgagtacagg ccagggctgg tatgacatgg cacgtacagc catcatgacc    60
tcgcgcgcat gttactacgt cgcgtcagat gaatcgacgc cttcctcgct gcaaatgtat   120
gcaacctcca gcagcaaaga tgttaccctg accgcaaagg acaagtttaa acagaatttg   180
cgtacggaga gtgactcccc gcacatcatg ggaatctggg agttgggtca ggggcctcgt   240
cagaaggtat ggaacatgtg gtatacaact ttttcgtacg gctcagcaaa atgcagcttg   300
aaagtgtcgg caggtccgcg cgtgctggag ccggtccgc agcagctgca agtccagtct   360
```

<210> SEQ ID NO 12
<211> LENGTH: 321
<212> TYPE: DNA
<213> ORGANISM: Artificial Sequence
<220> FEATURE:
<223> OTHER INFORMATION: Synthetic Construct

<400> SEQUENCE: 12

```
aaacttgagt tgaagaccgg tgccggcttc accttaccga ccagttatca tcaacaatgc    60
tattacgtgg ccctggacga agcacaggtg aattcaatta cgtttacgtt tgataccggc   120
tctggcagcg gtacatttcg tgatcccgtg ggcacttacc gctattcggc gagttatatc   180
ttgctgaaac cttcccaagg tccgaaacag cagtactggg cggttggcac cattgtagac   240
caatcagcca aatgtacaat ctcggttcgc gatggtgtca gtacgtcgat gtctaagcag   300
tcacagacaa tggttatcga t                                              321
```

<210> SEQ ID NO 13
<211> LENGTH: 120
<212> TYPE: PRT
<213> ORGANISM: Artificial Sequence
<220> FEATURE:
<223> OTHER INFORMATION: Synthetic Construct

<400> SEQUENCE: 13

Ser Val Thr Val Ser Thr Gly Gln Gly Trp Tyr Asp Met Ala Arg Thr
1               5                   10                  15

Ala Ile Met Thr Ser Arg Ala Cys Tyr Tyr Val Ala Ser Asp Glu Ser
            20                  25                  30

Thr Pro Ser Ser Leu Gln Met Tyr Ala Thr Ser Ser Ser Lys Asp Val

```
                35                  40                  45
Thr Leu Thr Ala Lys Asp Lys Phe Lys Gln Asn Leu Arg Thr Glu Ser
 50                  55                  60

Asp Ser Pro His Ile Met Gly Ile Trp Glu Leu Gly Gln Gly Pro Arg
 65                  70                  75                  80

Gln Lys Val Trp Asn Met Trp Tyr Thr Thr Phe Ser Tyr Gly Ser Ala
                 85                  90                  95

Lys Cys Ser Leu Lys Val Ser Ala Gly Pro Arg Val Leu Glu Ala Gly
                100                 105                 110

Pro Gln Gln Leu Gln Val Gln Ser
        115                 120

<210> SEQ ID NO 14
<211> LENGTH: 107
<212> TYPE: PRT
<213> ORGANISM: Artificial Sequence
<220> FEATURE:
<223> OTHER INFORMATION: Synthetic Construct

<400> SEQUENCE: 14

Lys Leu Glu Leu Lys Thr Gly Ala Gly Phe Thr Leu Pro Thr Ser Tyr
 1               5                  10                  15

His Gln Gln Cys Tyr Tyr Val Ala Leu Asp Glu Ala Gln Val Asn Ser
                20                  25                  30

Ile Thr Phe Thr Phe Asp Thr Gly Ser Gly Ser Gly Thr Phe Arg Asp
                35                  40                  45

Pro Val Gly Thr Tyr Arg Tyr Ser Ala Ser Tyr Ile Leu Leu Lys Pro
 50                  55                  60

Ser Gln Gly Pro Lys Gln Gln Tyr Trp Ala Val Gly Thr Ile Val Asp
 65                  70                  75                  80

Gln Ser Ala Lys Cys Thr Ile Ser Val Arg Asp Gly Val Ser Thr Ser
                 85                  90                  95

Met Ser Lys Gln Ser Gln Thr Met Val Ile Asp
                100                 105

<210> SEQ ID NO 15
<211> LENGTH: 18
<212> TYPE: DNA
<213> ORGANISM: Artificial Sequence
<220> FEATURE:
<223> OTHER INFORMATION: Synthetic Construct

<400> SEQUENCE: 15
catcaccatc atcaccac                                               18

<210> SEQ ID NO 16
<211> LENGTH: 6
<212> TYPE: PRT
<213> ORGANISM: Artificial Sequence
<220> FEATURE:
<223> OTHER INFORMATION: Synthetic Construct

<400> SEQUENCE: 16

His His His His His His
 1               5

<210> SEQ ID NO 17
<211> LENGTH: 348
<212> TYPE: DNA
<213> ORGANISM: Artificial Sequence
<220> FEATURE:
```

<223> OTHER INFORMATION: Synthetic Construct

<400> SEQUENCE: 17

```
agtagcgtga ctgttctgac gggacagggt tggtatgagt cttggggttc ctccggcgcg      60
tgttactatg ttgcgaccga tgaagcgcgc ttgagcaata tgcaactgta ccttactaac     120
aagagtaatg accgttccat cacgtttcgg ggcaaagtta gcgacgcata taatacctca     180
ggtggcagcg ggtctatcgc aagcgtctgg gagctcggta aaggcccccgc acaacgtgtg    240
tggagtatgg cttacagtag ctttactttc ggatctgctg catgctccct gcgcctgtcc     300
ggagggccac aggttctggg tggtggcagt gaactggtcc aggtggag                  348
```

<210> SEQ ID NO 18
<211> LENGTH: 336
<212> TYPE: DNA
<213> ORGANISM: Artificial Sequence
<220> FEATURE:
<223> OTHER INFORMATION: Synthetic Construct

<400> SEQUENCE: 18

```
tcaaatcacg cctacaaaat tgaagtgaaa acggggggcg gtagtacgtt gccgtattcc      60
caccatcagc tgtgttatta tacagcattc gacgagcctc aattatcatc tgttatcctg    120
accttcgaaa ccggatctgg ctctgggacg ttccggtctc cggtgggctc ccagctgaac    180
tcagccgcgt atattctgcg caaaccagcg aaagggccga acaacagta ctgggccctg     240
aacaatcgca ttggacagtc ggcccgttgc acgatcaccg tccgggacgg agtcagtgcg    300
agcctgagtt ccccgtcgca gaccatgcag attgat                              336
```

<210> SEQ ID NO 19
<211> LENGTH: 116
<212> TYPE: PRT
<213> ORGANISM: Artificial Sequence
<220> FEATURE:
<223> OTHER INFORMATION: Synthetic Construct

<400> SEQUENCE: 19

```
Ser Ser Val Thr Val Leu Thr Gly Gln Gly Trp Tyr Glu Ser Trp Gly
1               5                   10                  15

Ser Ser Gly Ala Cys Tyr Tyr Val Ala Thr Asp Glu Ala Arg Leu Ser
            20                  25                  30

Asn Met Gln Leu Tyr Leu Thr Asn Lys Ser Asn Asp Arg Ser Ile Thr
        35                  40                  45

Phe Arg Gly Lys Val Ser Asp Ala Tyr Asn Thr Ser Gly Gly Ser Gly
    50                  55                  60

Ser Ile Ala Ser Val Trp Glu Leu Gly Lys Gly Pro Ala Gln Arg Val
65                  70                  75                  80

Trp Ser Met Ala Tyr Ser Ser Phe Thr Phe Gly Ser Ala Ala Cys Ser
                85                  90                  95

Leu Arg Leu Ser Gly Gly Pro Gln Val Leu Gly Gly Ser Glu Leu
            100                 105                 110

Val Gln Val Glu
        115
```

<210> SEQ ID NO 20
<211> LENGTH: 112
<212> TYPE: PRT
<213> ORGANISM: Artificial Sequence
<220> FEATURE:
<223> OTHER INFORMATION: Synthetic Construct

<400> SEQUENCE: 20

```
Ser Asn His Ala Tyr Lys Ile Glu Val Lys Thr Gly Gly Gly Ser Thr
1               5                   10                  15

Leu Pro Tyr Ser His His Gln Leu Cys Tyr Tyr Thr Ala Phe Asp Glu
            20                  25                  30

Pro Gln Leu Ser Ser Val Ile Leu Thr Phe Glu Thr Gly Ser Gly Ser
        35                  40                  45

Gly Thr Phe Arg Ser Pro Val Gly Ser Gln Leu Asn Ser Ala Ala Tyr
    50                  55                  60

Ile Leu Arg Lys Pro Ala Lys Gly Pro Lys Gln Gln Tyr Trp Ala Leu
65              70                  75                  80

Asn Asn Arg Ile Gly Gln Ser Ala Arg Cys Thr Ile Thr Val Arg Asp
            85                  90                  95

Gly Val Ser Ala Ser Leu Ser Ser Pro Ser Gln Thr Met Gln Ile Asp
            100                 105                 110
```

<210> SEQ ID NO 21
<211> LENGTH: 1545
<212> TYPE: DNA
<213> ORGANISM: Artificial Sequence
<220> FEATURE:
<223> OTHER INFORMATION: Synthetic Construct

<400> SEQUENCE: 21

```
gtggtgatga tggtgatggc tctgtacctg cagctgctgc ggacccgcct caagaacgcg    60
cgggccggct gataccttca gggaacattt ggccgaacca tagctgaagg tggtgtacca   120
catgttccac actttctggc gggggccctg gcccagttcc cagatgccca tgatatgtgg   180
gctatcgctt cggtgcgca gattctgttt aaatttgtct ttcgcagtca gagtcacgtc   240
ttttgaagag gaggtggcat acatttgcag agaggaaggg gtcgactcat cgctggccac   300
gtaatagcac gcccgcgatg tcataatcgc ggtccgtgcc atatcgtacc atccttggcc   360
cgtcgacacc gtcacggagc ccctccccc gctgccccca ccgccactac caccgccgcc   420
agagtcaatc accatggttt gggactgctt gctcatggag gtgctaactc cgtcgcgaac   480
tgaaattgta catttggcag actggtccac gatcgttccc accgcccagt actgctgttt   540
cggaccctga aaggtttca gaaggatata gcttgcacta taccggtacg tacctaccgg   600
atcacggaac gtaccgctgc ctgatcctgt atcaaggta aaggtaatag agttcacctg   660
cgcttcgtca agcgccacgt aatagcactg ctggtgatag ctcgtaggga gggtaaatcc   720
cgcacccgtc ttgagttcca gtttgtaggc gtgatttgac acaaacaggg actccgatgc   780
cgccgcgccc gctggccgc tcggcagcac ggtcagttta gtaccgccgc caaaaactgg   840
gccatttaag ctatcatccc atgcggcgca ataataatca gcttcatcct cgctctggag   900
acccgaaata gccagaaaag ccgaggtacc cgatttactg ccggaaaagc ggtcactaac   960
tccacttggc agcaaatcat catagtaaat cagcagtttc ggcgcttttc ccggcagttg  1020
ctgataccag ttcactgcgt tgttaccgat gttggagctg ctcccactac agctgatcgt  1080
gatcgactga cccggggaac ccgacaccga cgccggctgc gtaagcgctg actgactgcc  1140
acctccgccg ctgccaccgc caccagagcc gcccccacct gaactaacgg taacggtggt  1200
gccctgaccc cagtaatcga agtacgtacc atcacccagg ccacgatctt tagcgcaata  1260
gtaaacggcg gtatcttcgg cgcgcaggct attcatttgc aggtacaggg tattttttgct  1320
attgtcgcgg ctaatagtga agcgtccttt tactgagtcg gcataatatt tgttagaccc  1380
```

```
atcgtagcgg atgaacgcaa cccactccag acctttgcca ggcgcctgac gcacccaatg    1440
cataccataa gagctgaagg taaaacccga cgcggcacag ctcagacgca aagagccgcc    1500
cggcttgacc agaccgccac cggattcaac cagctgcact tgcat                   1545
```

<210> SEQ ID NO 22
<211> LENGTH: 5
<212> TYPE: PRT
<213> ORGANISM: Artificial Sequence
<220> FEATURE:
<223> OTHER INFORMATION: Synthetic Construct

<400> SEQUENCE: 22

Gly Gly Gly Gly Ser
1               5